US011911113B2

(12) United States Patent
Sramek et al.

(10) Patent No.: US 11,911,113 B2
(45) Date of Patent: Feb. 27, 2024

(54) ELECTROMAGNETIC TRACKING SURGICAL SYSTEM AND METHOD OF CONTROLLING THE SAME

(71) Applicant: Auris Health, Inc., Redwood City, CA (US)

(72) Inventors: Christopher Sramek, Half Moon Bay, CA (US); Gregory J. Kintz, Santa Cruz, CA (US); David S. Mintz, Los Altos Hills, CA (US); Alan Yu, Union City, CA (US)

(73) Assignee: Auris Health, Inc., Redwood City, CA (US)

( * ) Notice: Subject to any disclaimer, the term of this patent is extended or adjusted under 35 U.S.C. 154(b) by 434 days.

(21) Appl. No.: 17/162,709

(22) Filed: Jan. 29, 2021

(65) Prior Publication Data

US 2021/0153954 A1     May 27, 2021

Related U.S. Application Data

(63) Continuation of application No. 15/406,599, filed on Jan. 13, 2017, now Pat. No. 10,932,861.

(Continued)

(51) Int. Cl.
*A61B 34/20*     (2016.01)
*A61B 5/06*     (2006.01)
(Continued)

(52) U.S. Cl.
CPC .............. *A61B 34/20* (2016.02); *A61B 34/30* (2016.02); *A61G 7/05* (2013.01); *A61B 5/062* (2013.01); *A61B 2034/2051* (2016.02); *A61G 13/04* (2013.01); *A61G 13/06* (2013.01); *A61G 13/08* (2013.01); *A61G 2203/30* (2013.01)

(58) Field of Classification Search
CPC . A61B 34/20; A61B 34/34; A61B 2034/2051; A61B 5/062
See application file for complete search history.

(56) References Cited

U.S. PATENT DOCUMENTS 1,011,038 A     12/1911    Davenport
3,428,307 A     2/1969    Hunter et al.
(Continued)

OTHER PUBLICATIONS

Advisory Action for U.S. Appl. No. 15/406,599, dated Dec. 16, 2019, 3 pages.

(Continued)

*Primary Examiner* — Boniface N Nganga
(74) *Attorney, Agent, or Firm* — Chang & Hale LLP

(57) ABSTRACT

An electromagnetic (EM) system for tracking a surgical tool is provided. The system may comprise a plurality of subsets of field generator coils disposed along edge portions of a surgical bed. Each subset of field generator coils may be configured to generate a magnetic field within a control volume. The system may further comprise a position sensor disposed on a portion of the surgical tool. The position sensor may be configured to generate a sensor signal in response to the magnetic field when the position sensor is located inside the control volume. Additionally, the system may comprise an EM system controller configured to selectively activate one or more of the subsets of field generator coils based on the sensor signal.

20 Claims, 13 Drawing Sheets

Related U.S. Application Data

(60) Provisional application No. 62/278,925, filed on Jan. 14, 2016.

(51) Int. Cl.
| | | |
|---|---|---|
| *A61G 7/00* | (2006.01) | |
| *A61G 13/00* | (2006.01) | |
| *A61B 34/30* | (2016.01) | |
| *A61G 7/05* | (2006.01) | |
| A61G 13/06 | (2006.01) | |
| A61G 13/08 | (2006.01) | |
| A61G 13/04 | (2006.01) | |

(56) References Cited

U.S. PATENT DOCUMENTS

| | | | |
|---|---|---|---|
| 3,620,210 | A | 11/1971 | Annas et al. |
| 3,751,028 | A | 8/1973 | Scheininger et al. |
| 4,173,228 | A | 11/1979 | Steenwyk et al. |
| 5,253,647 | A | 10/1993 | Takahashi et al. |
| 5,318,025 | A | 6/1994 | Dumoulin et al. |
| 5,429,132 | A | 7/1995 | Guy et al. |
| 5,558,091 | A | 9/1996 | Acker et al. |
| 5,711,299 | A * | 1/1998 | Manwaring ............ A61B 34/20 600/117 |
| 5,727,553 | A | 3/1998 | Saad |
| 5,913,168 | A | 6/1999 | Moreau et al. |
| 6,004,271 | A | 12/1999 | Moore |
| 6,253,770 | B1 | 7/2001 | Acker et al. |
| 6,310,573 | B1 | 10/2001 | Samuelsson |
| 6,530,913 | B1 | 3/2003 | Giba et al. |
| 6,544,230 | B1 | 4/2003 | Flaherty et al. |
| 6,572,535 | B2 | 6/2003 | Watanabe et al. |
| 6,593,884 | B1 | 7/2003 | Gilboa et al. |
| 6,610,007 | B2 | 8/2003 | Belson et al. |
| 6,636,757 | B1 | 10/2003 | Jascob et al. |
| 6,669,709 | B1 | 12/2003 | Cohn et al. |
| 6,690,963 | B2 | 2/2004 | Ben-Haim et al. |
| 6,904,630 | B2 | 6/2005 | Al-Kassim et al. |
| 6,905,460 | B2 | 6/2005 | Wang et al. |
| 6,944,492 | B1 | 9/2005 | Persoons et al. |
| 7,371,210 | B2 | 5/2008 | Brock et al. |
| 7,789,874 | B2 | 9/2010 | Yu et al. |
| 8,146,874 | B2 | 4/2012 | Yu |
| 8,302,221 | B1 | 11/2012 | Camp, Jr. |
| 8,505,137 | B1 | 8/2013 | Gaines, Jr. |
| 8,706,193 | B2 | 4/2014 | Govari et al. |
| 8,932,207 | B2 | 1/2015 | Greenburg et al. |
| 8,968,333 | B2 | 3/2015 | Yu et al. |
| 9,226,687 | B2 | 1/2016 | Soper et al. |
| 9,301,726 | B2 | 4/2016 | Mackie et al. |
| 9,314,306 | B2 | 4/2016 | Yu |
| 9,326,822 | B2 | 5/2016 | Lewis et al. |
| 9,408,669 | B2 | 8/2016 | Kokish et al. |
| 9,452,018 | B2 | 9/2016 | Yu |
| 9,504,604 | B2 | 11/2016 | Alvarez |
| 9,561,083 | B2 | 2/2017 | Yu et al. |
| 9,566,201 | B2 | 2/2017 | Yu |
| 9,622,827 | B2 | 4/2017 | Yu et al. |
| 9,636,184 | B2 | 5/2017 | Lee et al. |
| 9,713,509 | B2 | 7/2017 | Schuh et al. |
| 9,727,963 | B2 | 8/2017 | Mintz et al. |
| 9,737,371 | B2 | 8/2017 | Romo et al. |
| 9,737,373 | B2 | 8/2017 | Schuh |
| 9,744,335 | B2 | 8/2017 | Jiang |
| 9,763,741 | B2 | 9/2017 | Alvarez et al. |
| 9,788,910 | B2 | 10/2017 | Schuh |
| 9,818,681 | B2 | 11/2017 | Machida |
| 9,844,412 | B2 | 12/2017 | Bogusky et al. |
| 9,867,635 | B2 | 1/2018 | Alvarez et al. |
| 9,918,681 | B2 | 3/2018 | Wallace et al. |
| 9,931,025 | B1 | 4/2018 | Graetzel et al. |
| 9,949,749 | B2 | 4/2018 | Noonan et al. |
| 9,955,986 | B2 | 5/2018 | Shah |
| 9,962,228 | B2 | 5/2018 | Schuh et al. |
| 9,974,501 | B2 | 5/2018 | Hartmann et al. |
| 10,016,900 | B1 | 7/2018 | Meyer et al. |
| 10,022,192 | B1 | 7/2018 | Ummalaneni |
| 10,136,959 | B2 | 11/2018 | Mintz et al. |
| 10,145,747 | B1 | 12/2018 | Lin et al. |
| 10,159,532 | B1 | 12/2018 | Ummalaneni |
| 10,231,793 | B2 | 3/2019 | Romo |
| 10,231,867 | B2 | 3/2019 | Alvarez et al. |
| 10,244,926 | B2 | 4/2019 | Noonan et al. |
| 10,285,574 | B2 | 5/2019 | Landey et al. |
| 10,299,870 | B2 | 5/2019 | Connolly et al. |
| 10,482,599 | B2 | 11/2019 | Mintz et al. |
| 10,524,866 | B2 | 1/2020 | Srinivasan et al. |
| 10,639,114 | B2 | 5/2020 | Schuh et al. |
| 10,667,875 | B2 | 6/2020 | DeFonzo et al. |
| 10,765,487 | B2 | 9/2020 | Ho et al. |
| 2001/0009976 | A1 | 7/2001 | Panescu et al. |
| 2001/0029366 | A1 | 10/2001 | Swanson et al. |
| 2001/0047133 | A1 | 11/2001 | Gilboa et al. |
| 2002/0065455 | A1 | 5/2002 | Ben-Haim et al. |
| 2002/0087169 | A1 | 7/2002 | Brock et al. |
| 2002/0095730 | A1 | 7/2002 | Al-Kassim et al. |
| 2002/0167313 | A1 | 11/2002 | Taimisto |
| 2002/0177789 | A1 | 11/2002 | Ferry et al. |
| 2003/0052785 | A1 | 3/2003 | Gisselberg et al. |
| 2003/0074011 | A1 | 4/2003 | Gilboa et al. |
| 2003/0129750 | A1 | 7/2003 | Schwartz |
| 2003/0135204 | A1 | 7/2003 | Lee et al. |
| 2004/0162480 | A1 | 8/2004 | Satragno et al. |
| 2004/0162487 | A1 | 8/2004 | Klingenbeck-Regn et al. |
| 2004/0172757 | A1 | 9/2004 | Somasundaram |
| 2004/0176751 | A1 | 9/2004 | Weitzner et al. |
| 2004/0193146 | A1 | 9/2004 | Lee et al. |
| 2004/0199072 | A1 | 10/2004 | Sprouse et al. |
| 2004/0220461 | A1 | 11/2004 | Schwartz |
| 2005/0143944 | A1 | 6/2005 | Cech et al. |
| 2005/0182295 | A1 | 8/2005 | Soper et al. |
| 2005/0197767 | A1 | 9/2005 | Nortrup |
| 2006/0116571 | A1 | 6/2006 | Maschke et al. |
| 2006/0185091 | A1 | 8/2006 | Jackson |
| 2006/0241397 | A1 | 10/2006 | Govari et al. |
| 2007/0016007 | A1 | 1/2007 | Govari et al. |
| 2007/0025527 | A1 | 2/2007 | Eichenseer |
| 2007/0049797 | A1 | 3/2007 | Yoshida et al. |
| 2007/0060879 | A1 | 3/2007 | Weitzner et al. |
| 2007/0208252 | A1 | 9/2007 | Makower |
| 2007/0244388 | A1 | 10/2007 | Sato et al. |
| 2008/0195109 | A1 | 8/2008 | Hunter et al. |
| 2008/0245946 | A1 | 10/2008 | Yu |
| 2008/0300592 | A1 | 12/2008 | Weitzner et al. |
| 2009/0054884 | A1 | 2/2009 | Farley et al. |
| 2009/0064413 | A1 | 3/2009 | Sliski et al. |
| 2009/0126113 | A1 | 5/2009 | Hejkal et al. |
| 2009/0139030 | A1 | 6/2009 | Yang et al. |
| 2010/0016757 | A1 | 1/2010 | Greenburg et al. |
| 2010/0319121 | A1 | 12/2010 | Polomsky et al. |
| 2010/0324412 | A1 | 12/2010 | Govari et al. |
| 2011/0066029 | A1 | 3/2011 | Lyu et al. |
| 2012/0053453 | A1 | 3/2012 | Graumann |
| 2012/0158011 | A1 | 6/2012 | Sandhu et al. |
| 2012/0172712 | A1 | 7/2012 | Bar-Tal |
| 2012/0174317 | A1 | 7/2012 | Saracen et al. |
| 2012/0241576 | A1 | 9/2012 | Yu |
| 2013/0158346 | A1 | 6/2013 | Soper et al. |
| 2013/0162775 | A1 | 6/2013 | Baumann et al. |
| 2014/0033432 | A1 | 2/2014 | Marle |
| 2014/0142591 | A1 | 5/2014 | Alvarez et al. |
| 2014/0276391 | A1 | 9/2014 | Yu |
| 2014/0276647 | A1 | 9/2014 | Yu |
| 2014/0276935 | A1 | 9/2014 | Yu |
| 2014/0277333 | A1 | 9/2014 | Lewis et al. |
| 2014/0277334 | A1 | 9/2014 | Yu et al. |
| 2014/0309649 | A1 | 10/2014 | Alvarez et al. |
| 2014/0350387 | A1 | 11/2014 | Siewerdsen et al. |
| 2014/0357984 | A1 | 12/2014 | Wallace et al. |
| 2014/0364870 | A1 | 12/2014 | Alvarez et al. |
| 2014/0379000 | A1 | 12/2014 | Romo et al. |
| 2015/0026889 | A1 | 1/2015 | Roselius et al. |
| 2015/0047125 | A1 | 2/2015 | Bae et al. |

(56) References Cited

U.S. PATENT DOCUMENTS

| | | |
|---|---|---|
| 2015/0051592 A1 | 2/2015 | Kintz |
| 2015/0101442 A1 | 4/2015 | Romo |
| 2015/0119638 A1 | 4/2015 | Yu et al. |
| 2015/0119686 A1* | 4/2015 | Govari .................. A61B 5/062 600/409 |
| 2015/0164594 A1 | 6/2015 | Romo et al. |
| 2015/0164596 A1 | 6/2015 | Romo et al. |
| 2015/0335480 A1 | 11/2015 | Alvarez et al. |
| 2016/0000627 A1 | 1/2016 | Jackson et al. |
| 2016/0001038 A1 | 1/2016 | Romo et al. |
| 2016/0100896 A1 | 4/2016 | Yu |
| 2016/0235946 A1 | 8/2016 | Lewis et al. |
| 2016/0270865 A1 | 9/2016 | Landey et al. |
| 2016/0287279 A1 | 10/2016 | Bovay et al. |
| 2016/0296294 A1 | 10/2016 | Moll et al. |
| 2016/0338785 A1 | 11/2016 | Kokish et al. |
| 2016/0354582 A1 | 12/2016 | Yu et al. |
| 2016/0374541 A1 | 12/2016 | Agrawal et al. |
| 2017/0007337 A1 | 1/2017 | Dan |
| 2017/0007343 A1 | 1/2017 | Yu |
| 2017/0065364 A1 | 3/2017 | Schuh et al. |
| 2017/0065365 A1 | 3/2017 | Schuh |
| 2017/0100199 A1 | 4/2017 | Yu et al. |
| 2017/0105804 A1 | 4/2017 | Yu |
| 2017/0119413 A1 | 5/2017 | Romo |
| 2017/0119481 A1 | 5/2017 | Romo et al. |
| 2017/0165011 A1 | 6/2017 | Bovay et al. |
| 2017/0172673 A1 | 6/2017 | Yu et al. |
| 2017/0202627 A1 | 7/2017 | Sramek et al. |
| 2017/0209073 A1 | 7/2017 | Sramek et al. |
| 2017/0215978 A1 | 8/2017 | Wallace et al. |
| 2017/0290631 A1 | 10/2017 | Lee et al. |
| 2017/0333679 A1 | 11/2017 | Jiang |
| 2017/0340396 A1 | 11/2017 | Romo et al. |
| 2017/0365055 A1 | 12/2017 | Mintz et al. |
| 2017/0367782 A1 | 12/2017 | Schuh et al. |
| 2018/0025666 A1 | 1/2018 | Ho et al. |
| 2018/0177556 A1 | 6/2018 | Noonan |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289431 A1 | 10/2018 | Draper et al. |
| 2018/0325499 A1 | 11/2018 | Landey et al. |
| 2018/0333044 A1 | 11/2018 | Jenkins |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000566 A1 | 1/2019 | Graetzel et al. |
| 2019/0000576 A1 | 1/2019 | Mintz et al. |
| 2019/0083183 A1 | 3/2019 | Moll et al. |
| 2019/0105776 A1 | 4/2019 | Ho et al. |
| 2019/0105785 A1 | 4/2019 | Meyer et al. |
| 2019/0107454 A1 | 4/2019 | Lin et al. |
| 2019/0110839 A1 | 4/2019 | Rafii-Tari et al. |
| 2019/0110843 A1 | 4/2019 | Ummalaneni |
| 2019/0151148 A1 | 5/2019 | Alvarez et al. |
| 2019/0167366 A1 | 6/2019 | Ummalaneni et al. |
| 2019/0175009 A1 | 6/2019 | Mintz et al. |
| 2019/0175062 A1 | 6/2019 | Rafii-Tari et al. |
| 2019/0175287 A1 | 6/2019 | Hill et al. |
| 2019/0175799 A1 | 6/2019 | Hsu et al. |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216550 A1 | 7/2019 | Eyre et al. |
| 2019/0216576 A1 | 7/2019 | Eyre et al. |
| 2019/0228525 A1 | 7/2019 | Mintz et al. |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1 | 10/2019 | Ummalaneni et al. |
| 2019/0298460 A1 | 10/2019 | Al-Jadda et al. |
| 2019/0298465 A1 | 10/2019 | Chin et al. |
| 2019/0328213 A1 | 10/2019 | Landey et al. |
| 2019/0336238 A1 | 11/2019 | Yu et al. |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0374297 A1 | 12/2019 | Wallace et al. |
| 2019/0375383 A1 | 12/2019 | Auer |
| 2019/0380787 A1 | 12/2019 | Ye et al. |
| 2019/0380797 A1 | 12/2019 | Yu et al. |
| 2020/0000533 A1 | 1/2020 | Schuh et al. |
| 2020/0022767 A1 | 1/2020 | Hill et al. |
| 2020/0039086 A1 | 2/2020 | Meyer et al. |
| 2020/0046434 A1 | 2/2020 | Graetzel et al. |
| 2020/0054408 A1 | 2/2020 | Schuh et al. |
| 2020/0060516 A1 | 2/2020 | Baez, Jr. |
| 2020/0093549 A1 | 3/2020 | Chin et al. |
| 2020/0093554 A1 | 3/2020 | Schuh et al. |
| 2020/0100845 A1 | 4/2020 | Julian |
| 2020/0100855 A1 | 4/2020 | Leparmentier et al. |
| 2020/0101264 A1 | 4/2020 | Jiang |
| 2020/0107894 A1 | 4/2020 | Wallace et al. |
| 2020/0121502 A1 | 4/2020 | Kintz |
| 2020/0146769 A1 | 5/2020 | Eyre et al. |
| 2020/0188043 A1 | 6/2020 | Yu et al. |
| 2020/0197112 A1 | 6/2020 | Chin et al. |
| 2020/0206472 A1 | 7/2020 | Ma et al. |
| 2020/0217733 A1 | 7/2020 | Lin et al. |
| 2020/0222134 A1 | 7/2020 | Schuh et al. |
| 2020/0237458 A1 | 7/2020 | DeFonzo et al. |
| 2020/0261172 A1 | 8/2020 | Romo et al. |
| 2020/0268459 A1 | 8/2020 | Noonan |
| 2020/0268460 A1 | 8/2020 | Tse et al. |

OTHER PUBLICATIONS

Final Rejection for U.S. Appl. No. 15/406,599, dated Oct. 8, 2019, 27 pages.

Non-Final Rejection for U.S. Appl. No. 15/406,599, dated Apr. 24, 2019, 13 pages.

Non-Final Rejection for U.S. Appl. No. 15/406,599, dated Jun. 22, 2020, 18 pages.

Notice of Allowance for U.S. Appl. No. 15/406,599, dated Nov. 11, 2020, 8 pages.

\* cited by examiner

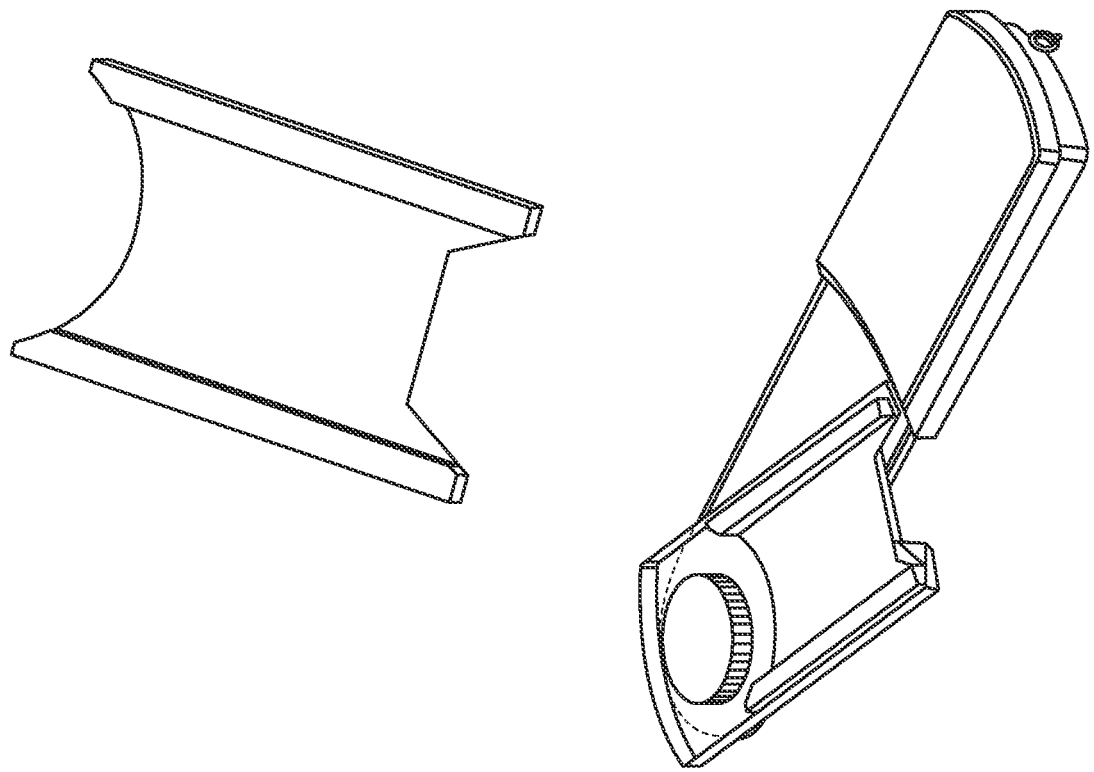
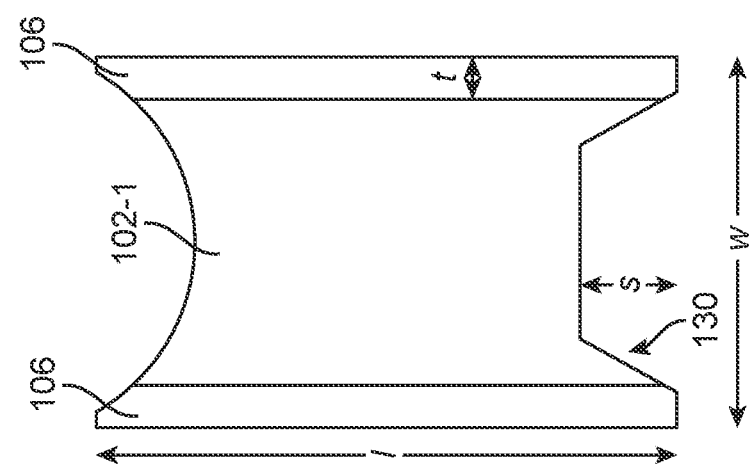
FIG. 10

ELECTROMAGNETIC TRACKING SURGICAL SYSTEM AND METHOD OF CONTROLLING THE SAME

CROSS-REFERENCE TO RELATED APPLICATIONS

This application is a continuation of U.S. patent application Ser. No. 15/406,599, filed Jan. 13, 2017, which claims the benefit of U.S. Provisional Patent Application Ser. No. 62/278,925, filed Jan. 14, 2016, each of which is hereby incorporated by reference in its entirety.

BACKGROUND

1. Field of the Invention

The field of the present application pertains to medical devices. More particularly, the field of the invention pertains to an electromagnetic tracking surgical system and a method of controlling the same.

2. Description of the Related Art

A surgical procedure may be performed on a patient using one or more surgical tools when the patient is placed on a surgical bed. The surgical tools may include endoscopes, catheters, ureteroscopes, or other similar devices. Endoscopy is a widely-used, minimally invasive technique for both imaging and delivering therapeutics to anatomical locations within the human body. Typically a flexible endoscope is used to deliver tools to an operative site inside the body—e.g., through small incisions or a natural orifice in the body—where a surgical procedure is to be performed. Endoscopes may have imaging, lighting, and steering capabilities at the distal end of a flexible shaft enabling navigation of non-linear lumens or pathways.

SUMMARY

In one aspect of the invention, an electromagnetic (EM) system for tracking a surgical tool is provided. A sensor associated with a surgical tool may be tracked based on interactions of the sensor with an electromagnetic field. In particular, a sensor associated with a surgical tool may be tracked when voltage is induced within a sensor coil that is placed within the electromagnetic field. In examples, the system provided may be used for alternating current (AC) EM tracking. In other examples, the system may be used for direct current (DC) EM tracking.

The electromagnetic field may be calibrated having a predetermined precision along a length of a surgical bed in the system. Small variations in position of the surgical device can be detected based on the sensor interaction with the electromagnetic field. The positional variations can have a spatial resolution of less than about 10 mm, 9 mm, 8 mm, 7 mm, 6 mm, 5 mm, 4 mm, 3 mm, 2 mm, 1 mm, or less than 1 mm. In some cases, the spatial resolution may be greater than about 10 mm.

The system may comprise a plurality of subsets of field generator coils disposed along edge portions of a surgical bed. Each subset of field generator coils may be configured to generate a magnetic field within a control volume. In some examples, the control volume may be static. In some examples, the control volume may be capable of changing dynamically (for example, but not limited to, time-variable). The system may further comprise a position sensor disposed on a portion of the surgical tool. The position sensor may be configured to generate a sensor signal in response to the magnetic field when the position sensor is located inside the control volume. Additionally, the system may comprise an EM system controller configured to selectively activate one or more of the subsets of field generator coils based on the sensor signal. In examples, a system may comprise more than one position sensor. In some examples, more than one position sensor may be capable of interacting with an electromagnetic field. In additional examples, one or more position sensors on a surgical tool having multiple position sensors may be activated at a time. In further examples, one or more position sensors on a surgical tool having multiple position sensors may be selectively activated. In some modes, multiple position sensors may be activated simultaneously. In some modes, position sensors may be activated one at a time. Additionally, an EM tracking surgical system may be capable of working in more than one mode. In these examples, a surgical system may switch between modes.

In some cases, a physician may need to know the spatial information of an endoscope relative to the patient's body, using the surgical bed as a datum. The spatial information may include a spatial position and/or orientation of the endoscope in a three-dimensional coordinate system. In some examples, spatial information received regarding an endoscope may be corroborated by additional sensor-based information. In particular, information regarding a spatial location of a sensor based on the sensor's interaction with an EM field may be corroborated by imaging information that is received from an imaging sensor, e.g., from a camera that is located on or near the surgical tool. One or more sensors may be attached to the endoscope to determine the spatial information. The sensors may include electromagnetic (EM) sensors configured to detect the spatial information of the endoscope, as well as movement of the endoscope, within the environment of the surgical bed. The EM sensors may be used in conjunction with a set of field generator coils that are disposed at or proximal to the surgical bed. The field generator coils may be configured to produce a calibrated (for example, but not limited to, known) electromagnetic (EM) field over a working volume proximal to the surgical bed. The working volume may be defined as a three-dimensional space above the surgical bed where a portion of the patient's body is located. A region of interest on the patient's body (for example, but not limited to, where a surgical procedure is to be performed) may be disposed within the working volume. When the endoscope moves within the working volume, the interaction of the EM sensors with the EM field results in electrical signals (for example, but not limited to, voltages) being generated. The spatial information and/or movement of the endoscope can be determined by analyzing the electrical signals.

Current state-of-the-art field generator coils may be provided in different configurations. For example, in some cases, a flat configuration of field generator coils may be placed in a surgical bed directly under a patient. Alternatively, a box configuration of generator coils may be placed externally on a side of the surgical bed or positioned above/over the patient. Optionally, a window configuration of generator coils may be positioned under the surgical bed or under the patient. However, each of the above configurations has certain deficiencies. For example, use of fluoroscopy may be limited in the flat configuration because the generator coils constitute radio-opaque objects/regions that can obstruct fluoroscopic imaging (for example, but not limited to, X-ray imaging). The box configuration may interfere with a physician's access to a patient since the coils are placed externally on the side of the surgical bed or positioned above/over the patient. In the window configuration, the positioning of coils under the surgical bed may result in mechanical and/or electromagnetic interference with other devices (for example, but not limited to, motors for actuating the bed, linear actuator drives, radio-frequency (RF) circuits, etc.) that are also disposed under the surgical bed. Additionally, the positioning of coils under the patient may require an overall thickness of the bed to be increased, which may result in larger form factor and higher manufacturing costs.

Additional drawbacks of one or more of the above coil configurations may include limited range of use. For example, the field generators in the above configurations typically generate a working volume of about 0.5 m×0.5 m×0.5 m, which is often insufficient to encompass a length or a width of a patient's body. In some instances, the surgical procedure may involve different parts of the patient's body that are spaced outside of the typical 0.5 m×0.5 m×0.5 m working volume. In those instances, movement of the coils around the surgical bed may be required, which may increase the mechanical complexity of the system and interfere with the physician's access to the patient.

Accordingly, it would be beneficial to have an integrated EM tracking surgical system and a method of controlling the system that provide improved navigation, ergonomics, and usability.

An electromagnetic (EM) system for tracking a surgical tool may be provided in accordance with another aspect of the invention. The system may comprise a plurality of subsets of field generator coils disposed along edge portions of a surgical bed. Each subset of field generator coils may be configured to generate a magnetic field within a control volume. A central portion of the surgical bed may be fluoroscopically transparent. The system may also comprise a position sensor disposed on a portion of the surgical tool. The position sensor may be configured to generate a sensor signal in response to the magnetic field when the position sensor is located inside the control volume. The system may further comprise an EM system controller configured to activate one or more of the subsets of field generator coils.

It shall be understood that different aspects of the invention can be appreciated individually, collectively, or in combination with each other. Other objects and features of the present invention will become apparent by a review of the specification, claims, and appended figures.

BRIEF DESCRIPTION OF THE DRAWINGS

The invention will be described, by way of example, and with reference to the accompanying drawings, in which:

FIG. 10 illustrates a reconfigurable bed portion of an EM tracking surgical system, in accordance with some embodiments;

DETAILED DESCRIPTION

Figure 1:
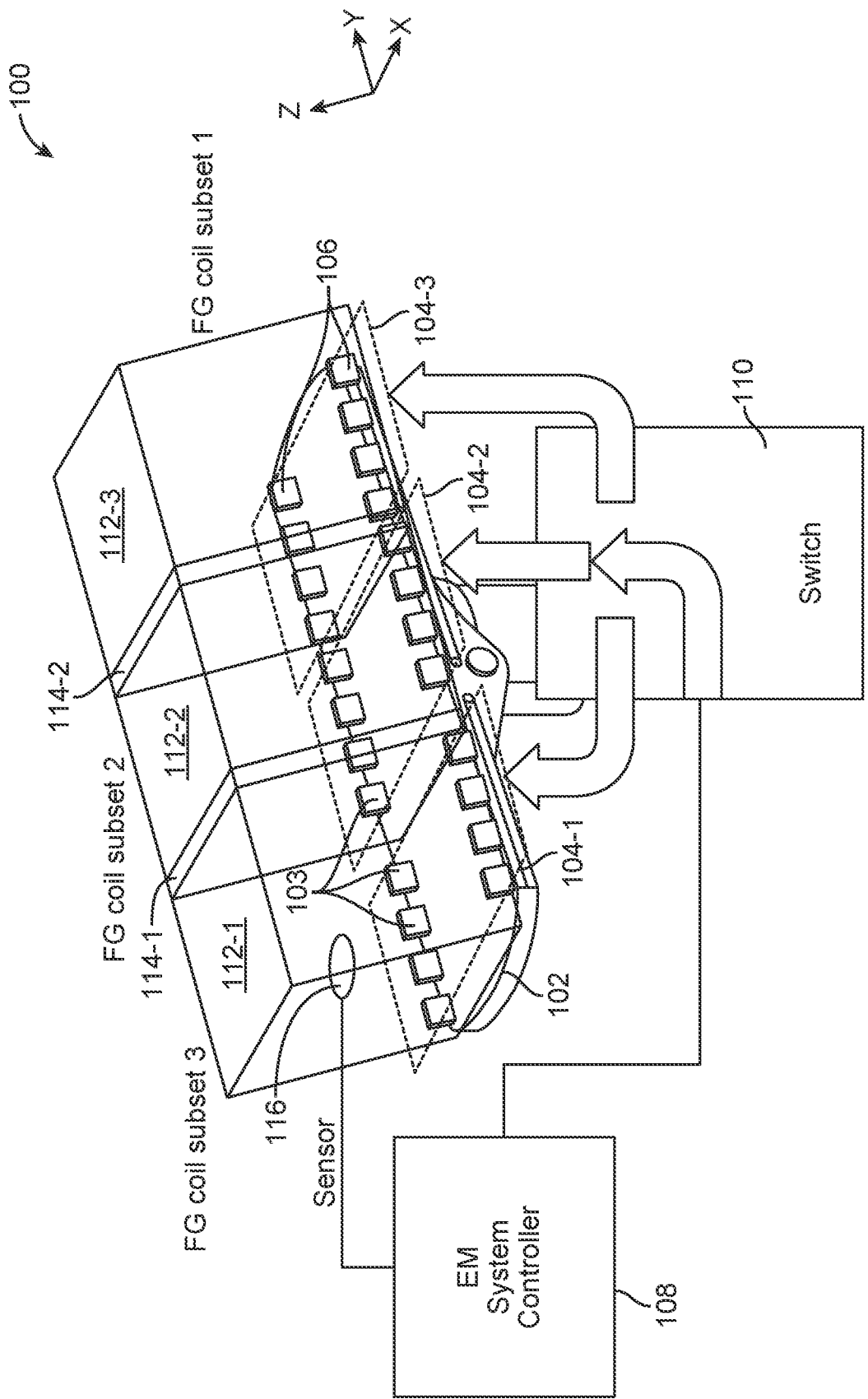
FIG. 1 illustrates a schematic of an electromagnetic (EM) tracking surgical system, in accordance with some embodiments.

Although certain preferred embodiments and examples are disclosed below, the inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

1. Overview

An electromagnetic (EM) tracking surgical system may be provided in which field generator coils are embedded along edge portions of a surgical bed. The placement of field generator coils in the disclosed configurations allows for unobstructed use of fluoroscopic imaging, and allows a physician to easily access the patient during a surgical procedure. Unlike some conventional systems, the field generator coils in the disclosed EM tracking surgical systems do not interfere with the physician's access to the patient. The integration of the field generator coils along the edge portions of the surgical bed also allows the surgical bed to remain compact since it does not increase the overall thickness of the surgical bed.

The disclosed configurations of field generator coils also allow a plurality of EM fields to be selectively activated within different working volumes above the surgical bed. The selective activation of EM fields within the different working volumes can prevent interfering EM fields from being generated, and can reduce EM interference between the field generator coils and other devices. Reduction in EM interference can improve the accuracy and sensitivity with which a surgical tool (for example, but not limited to, an endoscope having one or more EM sensors) can be tracked within the different working volumes above the surgical bed. Additionally, the disclosed configurations of field generator coils can extend the range of use of the system by a physician, since the working volumes can be configured to extend along a length of the surgical bed or in other configurations, depending on the requirements and complexity of the surgical procedure.

Tracking of a surgical tool can be facilitated by activating different subsets of field generator coils. In examples, different subsets of field generator coils may be activated depending on the location of the surgical procedure relative to the surgical bed. In some examples, as a surgical procedure progresses to different areas of a patient, field generator coils associated with different portions of the bed may be activated. Additionally, in examples, coils outside of the active subset(s) of field generator coils are inactive, thereby preventing interfering EM fields from being generated. In some examples, the working volumes above adjacent subsets of field generator coils may overlap so as to form a continuous global working volume along the length of the surgical bed.

2. System Components

FIG. 1 illustrates a schematic of an EM tracking surgical system, in accordance with some embodiments. As shown in FIG. 1, EM tracking surgical system 100 may comprise a surgical bed 102, a plurality of field generator coils 103, an EM system controller 108, a switch module 110, a plurality of working volumes 112, and a position sensor 116.

The surgical bed 102 may be configured to support a patient. A physician may perform a surgical procedure on the patient while the patient is placed on the surgical bed 102. In some embodiments, the surgical bed 102 may comprise multiple sections that are movable relative to one another. In those embodiments, the patient's body can be moved into different positions by moving different sections of the surgical bed 102 relative to one another. Alternatively, the surgical bed 102 may be formed monolithically as a single rigid structure.

The plurality of field generator coils 103 may be embedded or integrated along edge portions of the surgical bed 102. For example, as shown in FIG. 1, the plurality of field generator coils 103 may be embedded along a length of the surgical bed 102 in two rows 106. The rows 106 may extend parallel to each other along the edge of the surgical bed 102. As previously mentioned, the field generator coils 103 constitute radio-opaque objects/regions. Accordingly, the placement of the field generator coils 103 along the edges of the surgical bed 102 can allow unobstructed use of fluoroscopy to image the patient's body during a surgical procedure.

In some examples, the plurality of field generator coils 103 may be within one group of field generator coils that are associated with a working volume 112. The plurality of field generator coils 103 may include, and can be grouped into, subsets as field generator coils 104. For example, as shown in FIG. 1, the field generator coils 103 may include a first subset of field generator coils 104-1, a second subset of field generator coils 104-2, and a third subset of field generator coils 104-3. Although three subsets are illustrated in FIG. 1, it should be noted that the invention is not limited thereto, and that any number of subsets of field generator coils may be contemplated. In examples, field generator coils 103 may be grouped into 2, 3, 4, 5, 6, 7, 8, 9, 10, or more than 10 subsets.

Each subset of field generator coils 104 may comprise a number of field generator coils. In FIG. 1, each subset of field generator coils 104-1, 104-2, and 104-3 may comprise eight field generator coils. However, each subset of field generator coils need not be limited to eight field generator coils. In some embodiments, a subset of field generator coils may comprise more than eight field generator coils. For example, a subset of field generator coils may comprise 9, 10, 11, 12, 13, 14, 15, 16, 17, 18, 19, 20, 25, 30, 35, 40, or more than 40 field generator coils. In other embodiments, a subset of field generator coils may comprise less than eight field generator coils. For examples, a subset of field generator coils may comprise 1, 2, 3, 4, 5, 6, or 7 field generator coils. In some embodiments, different subsets of field generator coils may comprise different numbers of field generator coils. Any number of field generator coils within each subset, and between different subsets, may be contemplated.

The field generator coils within each subset may be fixed in place relative to one another. For example, the field generator coils may be spaced apart by a predetermined distance and/or at a predefined pitch along the edges of the surgical bed 102. Additionally, the subsets of field generator coils may be nominally fixed relative to the surgical bed 102 in a global coordinate system. Any portion of the surgical bed 102 may serve as an origin of the global coordinate system. In some embodiments, a datum point that lies substantially above a center portion of the surgical bed 102 may serve as the origin of the global coordinate system. In those embodiments, the positions of the subsets of field generator coils may be defined relative to the datum point.

In some embodiments, when the surgical bed comprises multiple sections that are movable relative to one another, the subsets of field generator coils may not be fixed in position relative to one another. Instead, the subsets of field generator coils may be located on one or more movable sections, and can move relative to one another when one or more sections of the surgical bed move. In those embodiments, global tracking of a surgical tool can be facilitated by adding sensors to the surgical bed that can detect changes in the configuration of the surgical bed.

As shown in FIG. 1, the plurality of working volumes 112 may include a first working volume 112-1, a second working volume 112-2, and a third working volume 112-3. Each working volume 112 may be associated with a subset of field generator coils, and may be disposed directly above the respective subset of field generator coils. For example, the first working volume 112-1 may be disposed directly above the first subset of field generator coils 104-1, the second working volume 112-2 may be disposed directly above the second subset of field generator coils 104-2, and the third working volume 112-3 may be disposed directly above the third subset of field generator coils 104-3.

In some embodiments, adjacent working volumes 112 may overlap each other to form an overlapping working volume 114. As shown in FIG. 1, a first overlapping working volume 114-1 may be formed by an overlapping region between the first working volume 112-1 and the second working volume 112-2. Similarly, a second overlapping working volume 114-2 may be formed by an overlapping region between the second working volume 112-2 and the third working volume 112-3. A size and/or shape of the overlapping working volumes 112 (i.e., the amount of overlap between adjacent working volumes) can be modified by adjusting the locations of the subsets of field generator coils. The size and/or shape of the overlapping working volumes can depend on the tolerance, sensitivity, position, and/or orientation of the field generator coils. The size and/or shape of the overlapping working volumes may be adjusted to optimize the magnetic flux uniformity therein, which can help to improve accuracy of the EM tracking. The overlapping working volumes may be symmetrical or non-symmetrical. The overlapping working volumes can have regular shapes or irregular shapes. Examples of regular shapes may include elliptical, cylindrical, or cubic shapes. In some alternative embodiments, the plurality of working volumes need not overlap. For example, adjacent subsets of field generator coils may be pulsed (for example, but not limited to, activated) sequentially such that the working volumes do not overlap. Alternatively, adjacent subsets of field generator coils may be orientated in a configuration that does not create overlapping working volumes. For example, adjacent subsets of field generator coils may not be disposed parallel to one another. Additionally, the working volumes may not overlap if adjacent subsets of field generator coils are spaced apart by at least a predefined distance. The predefined distance may be 1 m, 1.1 m, 1.2 m, 1.3 m, 1.4 m, 1.5 m, or greater than 1.5 m. Alternatively, the predefined distance may be less than 1 m. It should be noted that the amount of overlap between adjacent working volumes can affect the tracking performance of the system. For example, a large amount of overlap can provide continuously-joined working volumes, and ensure that the sensor can be tracked as it moves from one control volume to the next. However, a large amount of overlap may generate in-frequency noise which can impede tracking performance. Conversely, a small amount of overlap (or no overlap) can reduce in-frequency noise, but there is a risk of the system momentarily losing track of the sensor position as the sensor moves between control volumes.

The EM system controller 108 may be configured to provide electrical current pulses to the field generator coils 103 to generate an EM field over the respective working volume 112 above each subset of field generator coils 104. The EM system controller 108 can selectively activate (for example, but not limited to, power on) different subsets of field generator coils 104 to generate EM fields in different working volumes 112 by controlling one or more switches in the switch module 110. Electrical current pulses may be provided from the EM system controller 108 to the different subsets of field generator coils 104 via one or more switches in the switch module 110.

The switches may include electronic switches such as power MOSFETs, solid state relays, power transistors, and/or insulated gate bipolar transistors (IGBTs). Different types of electronic switches may be provided for controlling current to a subset of field generator coils. An electronic switch may utilize solid state electronics to control current flow. In some instances, an electronic switch may have no moving parts and/or may not utilize an electro-mechanical device (for example, but not limited to, traditional relays or switches with moving parts). In some instances, electrons or other charge carriers of the electronic switch may be confined to a solid state device. The electronic switch may optionally have a binary state (for example, but not limited to, switched-on or switched-off). The electronic switches may be used to control current flow to the subsets of field generator coils. The operation of switches to selectively activate one or more subsets of field generator coils 104 is described with reference to FIG. 3, below.

The EM system controller 108 can control the switches to activate: (1) the first subset of field generator coils 104-1 to generate an EM field in the first working volume 112-1, (2) the second subset of field generator coils 104-2 to generate an EM field in the second working volume 112-2, and/or (3) the third subset of field generator coils 104-3 to generate an EM field in the third working volume 112-3. In examples, the subsets of field generator coils may be activated simultaneously. In some examples, the subsets of field generator coils may be activated sequentially. For example, in some embodiments, the EM system controller 108 can simultaneously activate all three subsets of field generator coils 104 to create three separate EM fields in the respective working volumes 112. Alternatively, the EM system controller 108 can sequentially activate the first, second, and third subsets of field generator coils 104-1, 104-2, and 104-3 to sequentially generate EM fields in the first, second, and third working volumes 112-1, 112-2, and 112-3.

The EM system controller 108 can be configured to activate one or more subsets of field generator coils without activating one or more other subsets of field generator coils. For example, in some embodiments, the EM system controller 108 can activate only the first subset of field generator coils 104-1 without activating the second and third subsets of field generator coils 104-2 and 104-3. Similarly, the EM system controller 108 can activate only the second subset of field generator coils 104-2 without activating the first and third subsets of field generator coils 104-1 and 104-3. Likewise, the EM system controller 108 can activate only the third subset of field generator coils 104-3 without activating the first and second subsets of field generator coils 104-1 and 104-2. In some cases, the EM system controller 108 can activate the first and second subsets of field generator coils 104-1 and 104-2 without activating the third subset of field generator coils 104-3. In other cases, the EM system controller 108 can activate the second and third subsets of field generator coils 104-2 and 104-3 without activating the first subset of field generator coils 104-1. Optionally, the EM system controller 108 can activate the first and third subsets of field generator coils 104-1 and 104-3 without activating the second subset of field generator coils 104-2. Additional combinations (for example, but not limited to, of the activation) of different subsets of field generator coils may be contemplated.

As previously described, the EM system controller 108 can sequentially activate the first, second, and third subsets of field generator coils 104-1, 104-2, and 104-3. In some embodiments, all three subsets of field generator coils may continue to be powered on after they have been sequentially activated. For example, the first subset of field generator coils 104-1 may continue to be powered on after the second subset of field generator coils 104-2 has been activated. The first and second subsets of field generator coils 104-1 and 104-2 may continue to be powered on after the third subset of field generator coils 104-3 has been activated. Alternatively, in some embodiments, the first subset of field generator coils 104-1 may be powered off after the second subset of field generator coils 104-2 has been activated, and the second subset of field generator coils 104-2 may be powered off after the third subset of field generator coils 104-3 has been activated.

In some embodiments, the EM system controller 108 may be located on the surgical bed 102, for example on a base configured to support the surgical bed 102. In some embodiments, the EM system controller 108 may be located remotely from the surgical bed 102. For example, the EM system controller 108 may be disposed in a remote server that is in communication with the subsets of field generator coils 104 and the switch module 110. The EM system controller 108 may be software and/or hardware components included with the server. The server can have one or more processors and at least one memory for storing program instructions. The processor(s) can be a single or multiple microprocessors, field programmable gate arrays (FPGAs), or digital signal processors (DSPs) capable of executing particular sets of instructions. Computer-readable instructions can be stored on a tangible non-transitory computer-readable medium, such as a flexible disk, a hard disk, a CD-ROM (compact disk-read only memory), and MO (magneto-optical), a DVD-ROM (digital versatile disk-read only memory), a DVD RAM (digital versatile disk-random access memory), or a semiconductor memory. Alternatively, the program instructions can be implemented in hardware components or combinations of hardware and software such as, for example, ASICs, special purpose computers, or general purpose computers.

The EM system controller 108 may also be provided at any other type of external device (for example, but not limited to, a remote controller for controlling the surgical bed 102 and/or a surgical tool, any movable object or non-movable object, etc.). In some instances, the EM system controller 108 may be distributed on a cloud computing infrastructure. The EM system controller 108 may reside in different locations where the EM system controller 108 is capable of controlling the switch module 110 and selectively activating one or more subsets of field generator coils 104 based on the spatial information of the position sensor 116.

The position sensor 116 may be disposed in or on a portion of a surgical tool. For example, in some embodiments, the position sensor 116 may be disposed at a distal end of the surgical tool. Examples of surgical tools may include endoscopes, catheters, ureteroscopes, forceps, different types of scopes, or other similar devices or surgical accessories.

A position sensor, such as position sensor 116, may be configured to generate an electrical signal (for example, but not limited to, voltage or current signal) in response to EM fields generated by one or more subsets of field generator coils 104. Position sensor 116 may be an EM sensor. As position sensor 116 moves within a control volume 112, the interaction of the position sensor 116 with the EM field within the control volume 112 may cause electrical signals to be generated. The electrical signals may vary as the position sensor 116 moves between different locations within a control volume 112. Additionally, electrical signals may vary as the position sensor 116 moves between different control volumes. The EM system controller 108 may be configured to receive electrical signals from the position sensor 116. Additionally, the EM system controller 108 may analyze the signals to compute a local position of the sensor 116. The local position of the sensor 116 may be computed relative to a local coordinate system. The local coordinate system may be defined at an active subset of field generator coils 104 corresponding to the control volume 112 in which the position sensor 116 is located.

The EM system controller 108 may be further configured to compute a global position of the sensor 116 relative to a global coordinate system. The global coordinate system may be defined at the surgical bed 102 (for example, but not limited to, above a center portion of the surgical bed 102). The global position of the sensor 116 may be computed based on: (1) the local position of the sensor 116 within the control volume 112 above an active subset of field generator coils 104, and (2) the position of the active subset of field generator coils 104 relative to the surgical bed 102. The global position of the sensor 116 may be used to determine a position of a surgical tool relative to a patient on the surgical bed 102.

The EM system controller 108 may be configured to control the switch module 110 based on one or more inputs. The control of the switch module 110, and the selective activation of one or more subsets of field generator coils 104, may be manual and/or automatic.

In some embodiments, the EM system controller 108 may control the switch module 110 based on a user input corresponding to a selection of a region (or working volume 112) of the surgical bed 102 where tracking of a surgical tool is desired. For example, a physician may plan to perform a surgical procedure on a patient in a region within the first working volume 112-1. Accordingly, the physician or the physician's assistant may provide an input to the EM system controller 108 to activate the first subset of field generator coils 104-1, so that movement of the surgical tool can be tracked within the first control volume via the position sensor 116.

In some embodiments, the EM system controller 108 may control the switch module 110 based on an input indicative of the sensor position and/or movement within a control volume 112 above an active subset of field generator coils 104. For example, when the EM system controller 108 detects that the position sensor 116 is inside the first working volume 112-1 but outside of the first overlapping working volume 114-1, the EM system controller 108 may control the switch module 110 to activate only the first subset of field generator coils 104-1.

In some embodiments, when the EM system controller 108 detects that the position sensor 116 has moved into an overlapping working volume 114 between adjacent working volumes 112, the EM system controller 108 may control the switch module 110 to activate the subsets of field generator coils 104 corresponding to both working volumes 112 that have a portion within the overlapping working volume 114, so as to ensure that the position sensor 116 can continue to be tracked in the overlapping working volume 114 (for example, but not limited to, where the EM field strength may be lower). For example, when the EM system controller 108 detects that the position sensor 116 has moved into the first overlapping working volume 114-1, the EM system controller 108 may control the switch module 110 to activate both the first and second subsets of field generator coils 104-1 and 104-2 associated with working volumes 112-1 and 112-2, to ensure that the position sensor 116 can continue to be tracked in the first overlapping working volume 114-1.

In some embodiments, when the EM system controller 108 detects that the position sensor 116 has moved into the first overlapping working volume 114-1 and is moving from the first working volume 112-1 towards the second working volume 112-2, the EM system controller 108 may control the switch module 110 to activate both the first and second subsets of field generator coils 104-1 and 104-2 associated with working volumes 112-1 and 112-2, so as to ensure a smooth EM field transition (and in some examples but not limited to, continuous tracking/sensing) as the position sensor 116 moves between the first and second working volumes 112-1 and 112-2.

In some embodiments, when the EM system controller 108 detects that the position sensor 116 has moved into the second working volume 112-2 but outside of the first overlapping working volume 114-1, the EM system controller 108 may control the switch module 110 to activate the second subset of field generator coils 104-2 and power off the first subset of field generator coils 104-1. By selectively activating the subsets of field generator coils 104 based on the position and/or movement of the position sensor 116, interference between adjacent EM fields can be reduced or mitigated. Additionally, the energy needed to power the field generator coils 104 can be reduced, since not all of the field generator coils have to be powered on at the same time.

In some embodiments, the EM system controller 108 may control the switch module 110 based on an initialization input. The initialization input may cause the EM system controller 108 to control the switch module 110 to sequentially activate (for example, but not limited to, cycle through) the subsets of field generator coils 104, so as to determine: (1) whether the position sensor 116 is present in any of the control volumes 112, (2) in which control volume 112 the position sensor 116 is located if the position sensor 116 is detected, and (3) the position of the sensor 116 within the detected control volume 112. Accordingly, the EM system controller 108 can control the switch module 110 to activate the subset of field generator coils 104 corresponding to the control volume 112 in which the position sensor 116 is located, without activating the other subsets of field generator coils. If the position sensor 116 is determined to be in an overlapping working volume 114 between adjacent working volumes, the EM system controller 108 may control the switch module 110 to activate the subsets of field generator coils 104 corresponding to the adjacent working volumes 112.

During the sequential activation (for example, but not limited to, cycling) of the subsets of field generator coils 104, the local position of the sensor 116 relative to the local coordinate system of the working volume 112 (for example, but not limited to, where the sensor 116 is located) may be determined. The local position of the sensor 116 may be determined based on a distance between the sensor 116 and a reference point in the local coordinate system. The reference point may lie anywhere in the local coordinate system. For example, in some embodiments, the reference point may be at an origin of the local coordinate system. One or more subsets of field generator coils 104 may be activated based on the distance between the sensor 116 and the reference point.

For example, when the reference point is an origin of a local coordinate system that is defined at a center of a control volume 112, and the position sensor 116 is located at or near the reference point, only the subset of field generator coils corresponding to that control volume 112 may be activated. Conversely, when the position sensor 116 is located far away from the reference point such that the sensor 116 is proximate to another control volume 112, adjacent subsets of field generator coils 104 corresponding to both control volumes 112 may be activated. It should be noted that the local coordinate system need not be defined at the center of a control volume 112. In some other instances, the local coordinate system may be defined near an edge or corner of a control volume 112. Any placement of the reference point and/or the local coordinate system within a control volume 112 may be contemplated.

In some embodiments, the local position of the sensor 116 may be determined based on distances between the sensor 116 and a plurality of reference points in different local coordinate systems. The different local coordinate systems may lie in different control volumes 112. The EM system controller 108 may be configured to determine a minimum distance from those distances, and activate a subset of field generator coils 104 corresponding to the control volume 112 based on the minimum distance.

During a surgical procedure, the EM system controller 108 may be configured to track the position and/or movement of the sensor 116 within a control volume 112 corresponding to an active subset of field generator coils 104. As the position sensor 116 moves between adjacent control volumes 112, different subsets of field generator coils 104 may be selectively activated to ensure that the sensor 116 is continuously tracked, while at the same time reducing EM field interference effects.

2. Closed-Loop Positional and Speed Feedback

Figure 2:
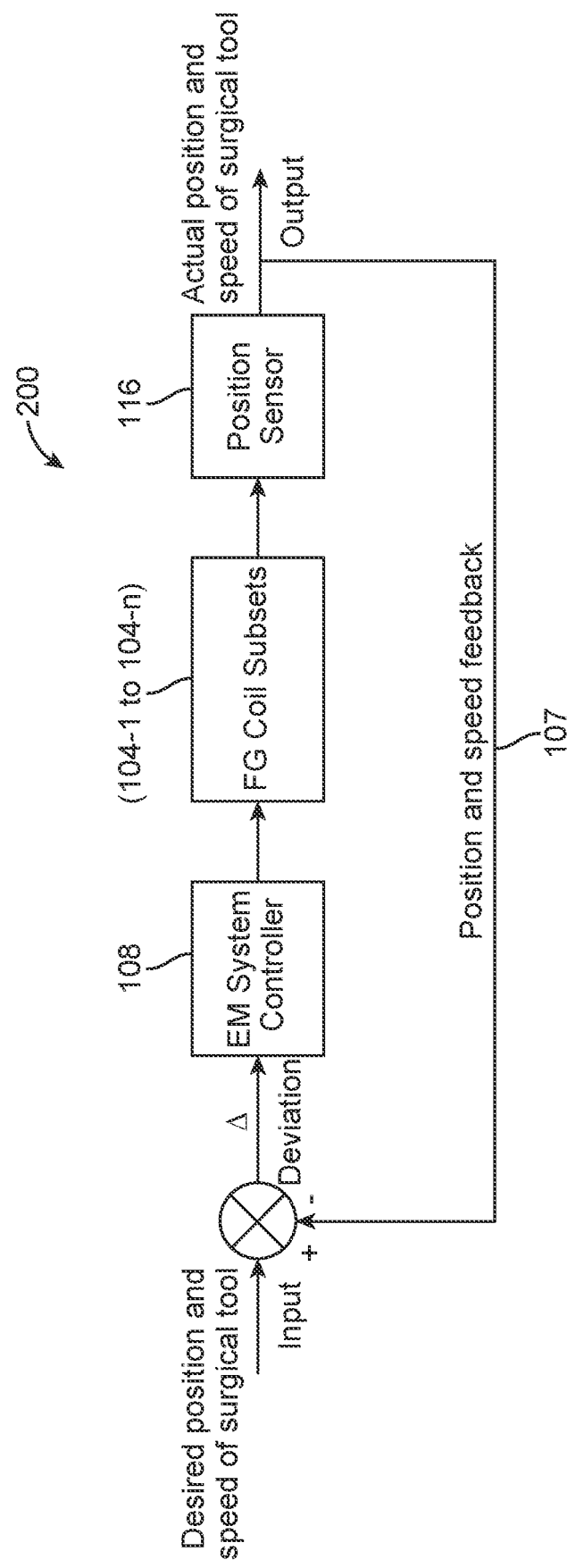
FIG. 2 illustrates a block diagram of a closed-loop control EM tracking surgical system, in accordance with some embodiments.

FIG. 2 illustrates a block diagram of a closed-loop control EM tracking surgical system, in accordance with some embodiments. As shown in FIG. 2, a closed-loop control EM tracking surgical system 200 may comprise an EM system controller 108, a plurality of subsets of field generator coils 104-1 through 104-n, and a position sensor 116 operably connected via a feedback loop 107. Any number (n) of subsets of field generator coils 104 may be contemplated, and may depend in part on the strength of each subset of field generator coils 104 and/or a size (for example, but not limited to, length and width) of a surgical bed (for example, but not limited to, surgical bed 102 of FIG. 1).

In FIG. 2, a surgical tool may be automatically controlled using one or more robotic arms that are in operable communication with the EM system controller 108. The EM system controller 108 may be configured to track and control the position and/or movement of the surgical tool, and selectively activate one or more subsets of field generator coils 104, based on positional and speed feedback of the position sensor 116 as the sensor 116 moves between different control volumes (for example, but not limited to, control volumes 112 of FIG. 1).

As shown in FIG. 2, an input may be initially provided to the EM tracking surgical system 200. The input may comprise a desired position and/or speed of a surgical tool. The position and/or speed of the surgical tool may be controlled using the one or more robotic arms. The EM system controller 108 may be configured to activate one or more subsets of field generator coils 104, and to determine a control volume (for example, but not limited to, control volume 112) in which the position sensor 116 is located. Once the control volume has been determined, the subset of field generator coils 104 corresponding to that control volume may be activated while the other subsets of field generator coils 104 may be powered off. As previously described, the selective activation of different subsets of field generator coils 104 can reduce EM field interference effects. The position and/or movement of the sensor 116 may be determined based on the interaction of the sensor 116 with the EM field within the control volume. The actual position and/or speed of the surgical tool may be determined based on the position and/or movement of the sensor 116, and may be compared against the input to determine an amount of deviation A (if any) from the desired position and/or speed of the surgical tool. The EM system controller 108 may be configured to adjust the actual position and/or speed of the surgical tool (for example, but not limited to, via the one or more robotic arms) based on the amount of deviation.

3. Switching Circuit

Figure 3:
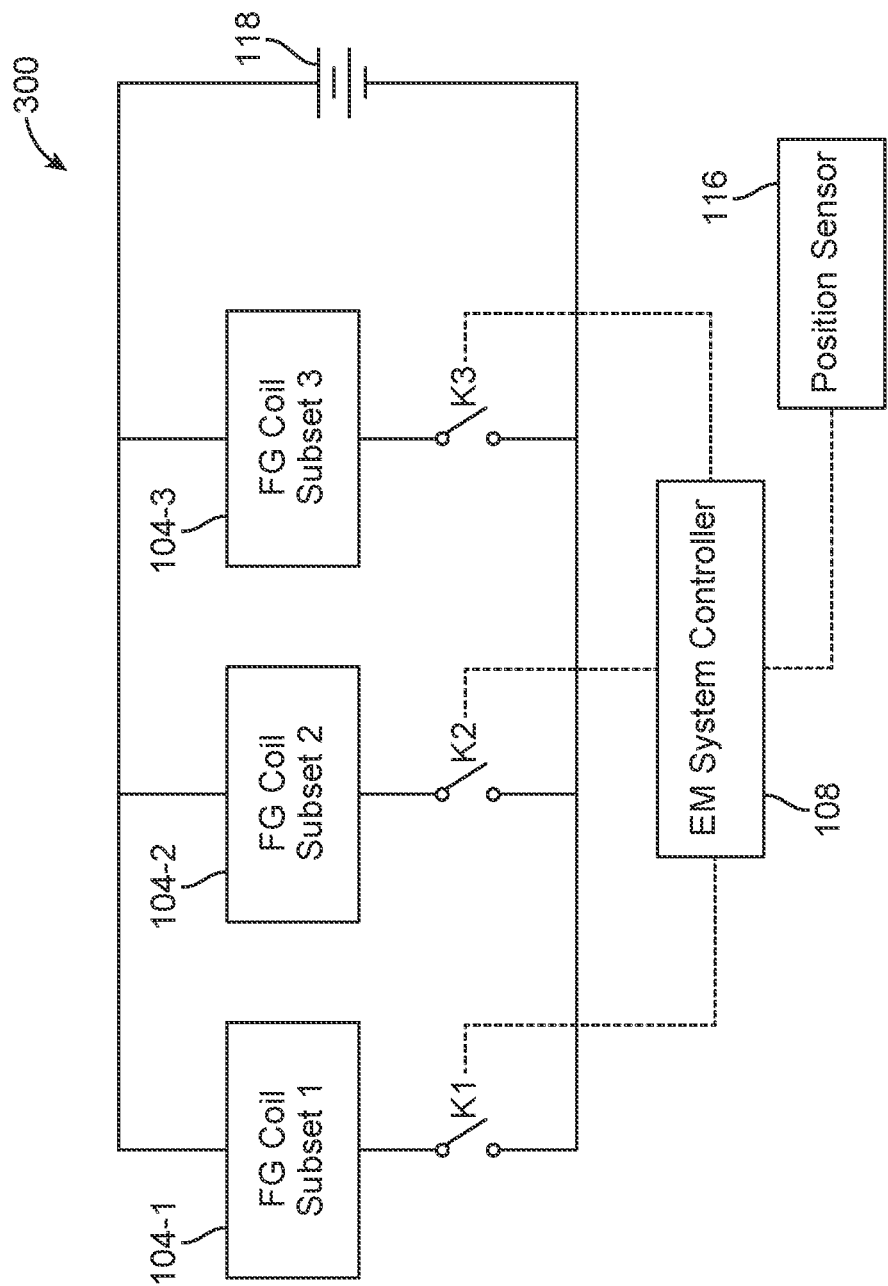
FIG. 3 illustrates a schematic circuit diagram of an EM tracking surgical system, in accordance with some embodiments.

FIG. 3 illustrates a schematic circuit diagram of an EM tracking surgical system, in accordance with some embodiments. As shown in FIG. 3, an EM tracking surgical system 300 may comprise a plurality of subsets of field generator coils 104-1, 104-2, and 104-3 electrically connected to a power supply 118. An EM system controller 108 may be in operable communication with a plurality of switches K1, K2, and K3 and a position sensor 116. The plurality of switches K1, K2, and K3 may be located in a switch module (for example, but not limited to, switch module 110 of FIG. 1). The EM system controller 108 may be configured to selectively activate one or more subsets of field generator coils 104, either simultaneously, sequentially, or in a round-robin configuration, based on a position and/or movement of the position sensor 116 within and/or between adjacent control volumes (for example, but not limited to, control volumes 112 of FIG. 1).

The EM system controller 108 may be configured to control one or more switches to selectively activate one or more subsets of field generator coils 104. For example, the EM system controller 108 may selectively activate the first subset of field generator coils 104-1 by closing the switch K1. Similarly, the EM system controller 108 may selectively activate the second subset of field generator coils 104-2 by closing the switch K2. Likewise, the EM system controller 108 may selectively activate the third subset of field generator coils 104-3 by closing the switch K3. In some embodiments, the EM system controller 108 may simultaneously activate two or more subsets of field generator coils 104. For example, the EM system controller 108 may simultaneously activate the first and second subsets of field generator coils 104-1 and 104-2 by closing the switches K1 and K2. Similarly, the EM system controller 108 may simultaneously activate the first and third subsets of field generator coils 104-1 and 104-3 by closing the switches K1 and K3. Likewise, the EM system controller 108 may simultaneously activate the second and third subsets of field generator coils 104-2 and 104-3 by closing the switches K2 and K3. Optionally, the EM system controller 108 may simultaneously activate the first, second, and third subsets of field generator coils 104-1, 104-2, and/or 104-3 by simultaneously closing the switches K1, K2, and/or K3, respectively. In some embodiments, the EM system controller 108 may sequentially close the switches K1, K2, and/or K3. In some other embodiments, the EM system controller 108 may close the switches K1, K2, and/or K3 in alternating manner. In some embodiments, the EM system controller 108 may close the switches K1, K2, and/or K3 at a same frequency or at different frequencies. In some embodiments, the EM system controller 108 may close/open the switches K1, K2, and/or K3 for different lengths of time, so as to activate or power off the subsets of field generator coils 104 for different lengths of time.

4. Layout of Field Generator Coils and Working Volumes

Figure 4:
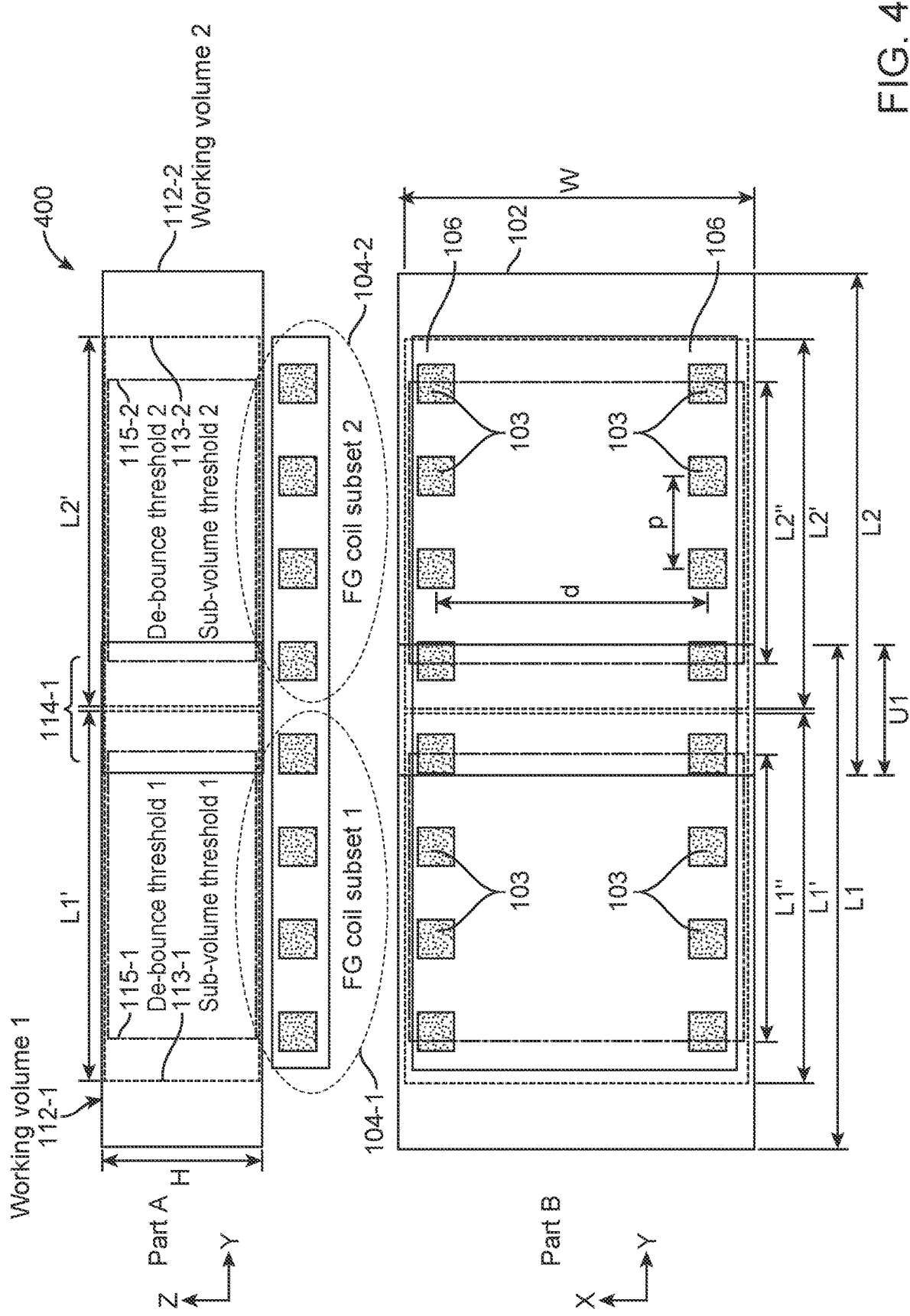
FIG. 4 illustrates schematic layouts of the field generator coils and working volumes within an EM tracking surgical system, in accordance with some embodiments.

FIG. 4 illustrates schematic layouts of the field generator coils and working volumes within an EM tracking surgical system, in accordance with some embodiments. Part A of FIG. 4 illustrates a schematic side view of a portion of an EM tracking surgical system 400, and Part B of FIG. 4 illustrates a schematic top view of the portion of the system 400.

As shown in FIG. 4, a first subset of field generator coils 104-1 and a second subset of field generator coils 104-2 may be embedded along a length portion of a surgical bed 102. A first working volume 112-1 may be defined above the first subset of field generator coils 104-1, and a second working volume 112-2 may be defined above the second subset of field generator coils 104-2. The dimensions of the first working volume 112-1 may be given by a length L1, a width W, and a height H. The dimensions of the second working volume 112-2 may be given by a length L2, a width W, and a height H. In some embodiments, the lengths L1 and L2 may be substantially the same. In other embodiments, the lengths L1 and L2 may be different. For example, in some instances, the length L1 may be less than the length L2. In other instances, the length L1 may be greater than the length L2. In some alternative embodiments (not shown), the widths of the first and second working volumes 112 may be different. Optionally, the heights of the first and second working volumes 112 may be different.

Each working volume 112 may comprise a sub-volume threshold located within each working volume. The sub-volume threshold is located at a boundary between overlapping working volumes. The sub-volume threshold may correspond to a transition zone as the sensor moves between overlapping working volumes. For example, the first working volume 112-1 may comprise a first sub-volume threshold 113-1, and the second working volume 112-2 may comprise a second sub-volume threshold 113-2. The first sub-volume threshold 113-1 may have a length L1', and the second sub-volume threshold 113-2 may have a length L2'. In some embodiments, the lengths L1' and L2' may be substantially the same. In other embodiments, the lengths L1' and L2' may be different. The widths of the first and second sub-volume thresholds may be the same, and the heights of the first and second sub-volume thresholds may be the same. In some alternative embodiments (not shown), the widths of the first and second sub-volume thresholds may be different. Optionally, the heights of the first and second sub-volume thresholds may be different.

Each working volume 112 may further comprise a de-bounce threshold located within each sub-volume threshold. For example, the first working volume 112-1 may comprise a first de-bounce threshold 115-1, and the second working volume 112-2 may comprise a second de-bounce threshold 115-2. The second working volume may be activated once the sensor leaves the first de-bounce threshold and enters the second de-bounce threshold. Similarly, the first working volume may be activated once the sensor leaves the second de-bounce threshold and enters the first de-bounce threshold. Accordingly, the de-bounce thresholds may serve as "de-bouncing switches" for determining which working volume is to be activated. The first de-bounce threshold 115-1 may have a length L1", and the second de-bounce threshold 115-2 may have a length L2". In some embodiments, the lengths L1" and L2" may be substantially the same. In other embodiments, the lengths L1" and L2" may be different. The widths of the first and second de-bounce thresholds may be the same, and the heights of the first and second de-bounce thresholds may be the same. In some alternative embodiments (not shown), the widths of the first and second de-bounce thresholds may be different. Optionally, the heights of the first and second de-bounce thresholds may be different.

As shown in FIG. 4, the first and second working volumes may overlap so as to form a first overlapping working volume 114-1 disposed at a boundary between the first and second subsets of field generator coils 104-1 and 104-2. The first and second working volumes 112-1 and 112-2 may overlap by various amounts. For example, the first and second working volumes 112-1 and 112-2 may overlap by 1%, 2%, 5%, 10%, 15%, 20%, 25%, 30%, or more than 30%. The first and second working volumes 112-1 and 112-2 may be configured to overlap such that the position sensor 116 can be accurately tracked and controlled near the boundaries of the control volumes 112, and as the position sensor 116 moves between adjacent working volumes 112. The first overlapping working volume 114-1 may have a length U1, a width W, and a height H.

Each subset of field generator coils 104 may comprise a number of field generator coils 103. The number of field generator coils 103 in the subsets may be same or different. As shown in part B of FIG. 4, each subset of field generator coils 104 may comprise eight field generator coils 103. The field generator coils 103 may be disposed along the edges of the surgical bed 102 in two parallel rows 106. The field generator coils 103 may be spaced apart from one another along each row 106, at a pitch p in the Y-direction. Laterally opposite field generator coils 103 in the two rows 106 may be spaced apart by a distance d from each other in the X-direction. The field generator coils 103 in the subsets 104 may be spaced in a configuration that allows an EM field of a predetermined strength to substantially extend over each working volume 112.

5. Selective Activation of Field Generator Coils with One Position Sensor

Figure 5:
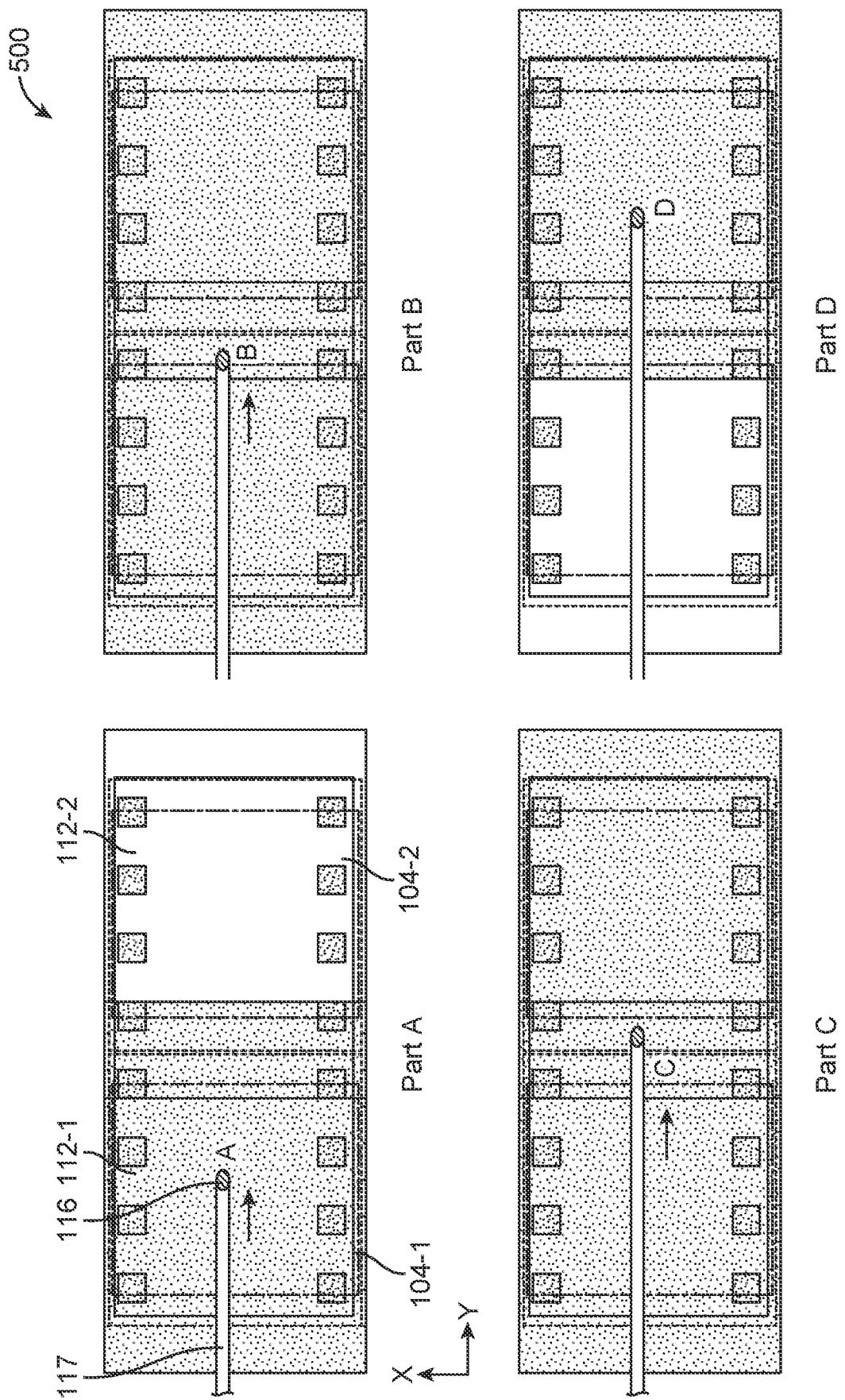
FIG. 5 illustrates selective activation of field generator coils and working volumes as a surgical tool comprising a position sensor that moves within an EM tracking surgical system, in accordance with some embodiments.

FIG. 5 illustrates selective activation of field generator coils and working volumes as a surgical tool comprising a position sensor that moves within an EM tracking surgical system, in accordance with some embodiments. Parts A, B, C, and D of FIG. 5 illustrate schematic top views of a portion of an EM tracking surgical system 500.

As shown in part A of FIG. 5, a position sensor 116 may be disposed at a distal end of a surgical tool 117. The surgical tools may include endoscopes, catheters, ureteroscopes, or other similar devices. Initially, the surgical tool 117 may be positioned such that the position sensor 116 is located at position A. Position A may be a point within a first working volume 112-1 above a first subset of field generator coils 104-1. An EM system controller (for example, but not limited to, EM system controller 108) may detect that the position sensor 116 is within the first working volume 112-1 and not in the second working volume 112-2. Additionally, the EM system controller may detect that the position sensor 116 is within the first working volume 112-1 but outside of a first overlapping working volume 114-1. The first overlapping working volume 114-1 may be an overlapping region between the first and second working volumes 112-1 and 112-2. Accordingly, the EM system controller may selectively activate the first subset of field generator coils 104-1 without activating the second subset of field generator coils 104-2. When the first subset of field generator coils 104-1 is activated, the first working volume 112-1 may become an active working volume, as indicated by the shaded region over the first working volume 112-1.

During a surgical procedure, the surgical tool 117 may move to a different location, such that the position sensor 116 may move to position B shown in part B of FIG. 5. Position B may be a point that lies within the first working volume 112-1 and the first overlapping working volume 114-1. Since position B lies near the boundary of the first working volume 112-1, the EM system controller may activate the second subset of field generator coils 104-2 in addition to the first subset of field generator coils 104-1, to ensure that the position sensor 116 can be accurately tracked near the boundary between adjacent working volumes 112. When the first and second subset of field generator coils 104-1 and 104-2 are activated, the first and second working volumes 112-1 and 112-2 become active working volumes, as indicated by the shaded regions over the first and second working volumes 112-1 and 112-2.

Next, the surgical tool 117 may move to a different location, such that the position sensor 116 may move to position C shown in part C of FIG. 5. Position C may be another point in the first overlapping working volume 114-1. However, unlike position B, position C may lie within the second working volume 112-2. Since position C lies near the boundary of the second working volume 112-2, the EM system controller may continue to activate both the first and second subsets 112, to ensure that the position sensor 116 can be accurately tracked near the boundary between adjacent working volumes 112.

Next, the surgical tool 117 may move to a different location, such that the position sensor 116 may move to position D shown in part D of FIG. 5. The EM system controller may detect that the position sensor 116 is within the second working volume 112-2 but outside of the first overlapping working volume 114-1. Accordingly, the EM system controller may continue to activate the second subset of field generator coils 104-2, but power off the first subset of field generator coils 104-1.

Figure 6:
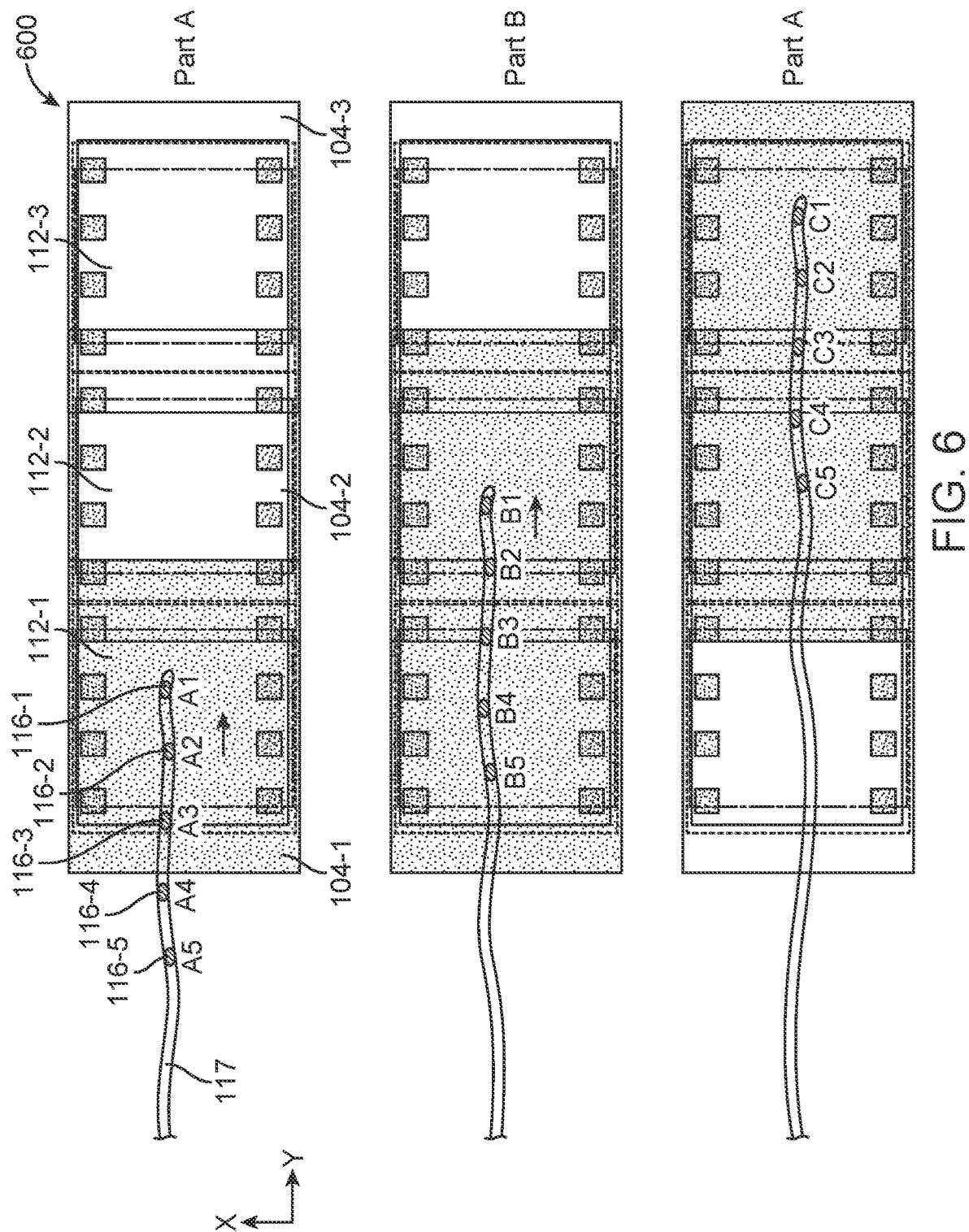
FIG. 6 illustrates selective activation of field generator coils and working volumes as a surgical tool comprising a plurality of position sensors that move within an EM tracking surgical system, in accordance with some embodiments.

6. Selective Activation of Field Generator Coils with a Plurality of Position Sensors FIG. 6 illustrates selective activation of field generator coils and working volumes as a surgical tool comprising a plurality of position sensors that move within an EM tracking surgical system, in accordance with some embodiments. Parts A, B, and C of FIG. 6 illustrate schematic top views of a portion of an EM tracking surgical system 600. The embodiment of FIG. 6 has similarities to the embodiment of FIG. 5.

In FIG. 6, a surgical tool 117 may be a flexible probe or shaft capable of twisting and bending about different directions. Additionally, the surgical tool 117 may comprise a plurality of position sensors 116 that include position sensors 116-1, 116-2, 116-3, 116-4, and 116-5. For example, a position sensor 116-1 may be disposed at a distal end of the surgical tool 117, and a plurality of position sensors 116-2, 116-3, 116-4, and 116-5 may be spaced apart along a length of the surgical tool 117. By placing the plurality of position sensors 116 at different locations along the surgical tool 117, the position/orientation/shape of the surgical tool 117 can be determined through use of an EM field, which may be important during a surgical procedure as the tool 117 is being inserted into a patient's body. In some cases, the position/orientation/shape of the surgical tool 117 that is obtained by an EM system controller can be mapped onto the fluoroscopic image of the patient's body in real-time as the surgical procedure is being performed.

Additionally, in FIG. 6, more than two working volumes may be provided. For example, the EM tracking surgical system 600 may comprise three working volumes 112: a first working volume 112-1, a second working volume 112-2, and a third working volume 112-3. In examples, 4, 5, 6, 7, 8, 9, 10, or more than 10 working volumes 112 may be provided.

As shown in part A of FIG. 6, the position sensors 116-1, 116-2, 116-3, 116-4, and 116-5 may be located at positions A1, A2, A3, A4, and A5, respectively. Positions A1, A2, and A3 may lie within the first working volume 112-1 above a first subset of field generator coils 104-1. Positions A4 and A5 may lie outside of the first working volume 112-1 and/or any working volume. An EM system controller (for example, but not limited to, EM system controller 108 of FIG. 1) may detect that the position sensors 116-1, 116-2, and 116-3 are within the first working volume 112-1, and not in the second and third working volumes 112-2 and 112-3. Additionally, the EM system controller may detect that the position sensors 116-1, 116-2, and 116-3 are within the first working volume 112-1 outside of a first overlapping working volume 114-1. Accordingly, the EM system controller may selectively activate the first subset of field generator coils 104-1 without activating the second subset of field generator coils 104-2.

During a surgical procedure, the surgical tool 117 may move from the position shown in part A to the position shown in part B of FIG. 6. Referring to part B of FIG. 6, the position sensors 116-1, 116-2, 116-3, 116-4, and 116-5 may be located at positions B1, B2, B3, B4, and B5, respectively. Position B1 may be a point that lies within the second working volume 112-2 outside of the first overlapping working volume 114-1. Position B2 may be a point that lies within the second working volume 112-2 and the first overlapping working volume 114-1. Position B3 may be a point that lies within the first working volume 112-1 and the first overlapping working volume 114-1. Positions B4 and B5 may be different points that lie within the first working volume 112-1 outside of the first overlapping working volume 114-1. Accordingly, the EM system controller may activate the second subset of field generator coils 104-2 in addition to the first subset of field generator coils 104-1, to ensure that the position sensor 116 can be accurately tracked within the first and the second working volumes 112-1 and 112-2.

Next, the surgical tool 117 may move from the position shown in part B to the position shown in part C of FIG. 6. Referring to part C of FIG. 6, the position sensors 116-1, 116-2, 116-3, 116-4, and 116-5 may be located at positions C1, C2, C3, C4, and C5, respectively. Positions C1 and C2 may be different points that lie within the third working volume 112-3 outside of a second overlapping working volume 114-2. Position C3 may be a point that lies within the third working volume 112-3 and the second overlapping working volume 114-2. Positions C4 and C5 may be different points that lie within the second working volume 112-2 outside of the second overlapping working volume 114-2. None of the positions C1-05 lies within the first working volume 112-1 and/or the first overlapping working volume 114-1. Accordingly, the EM system controller may activate the third subset of field generator coils 104-3 in addition to the second subset of field generator coils 104-2, to ensure that the position sensor 116 can be accurately tracked within the second and the third working volumes. Additionally, the EM system controller may power off the first subset of field generator coils 104-1 since none of the position sensors 116 lies within the first working volume 112-1.

Figure 7:
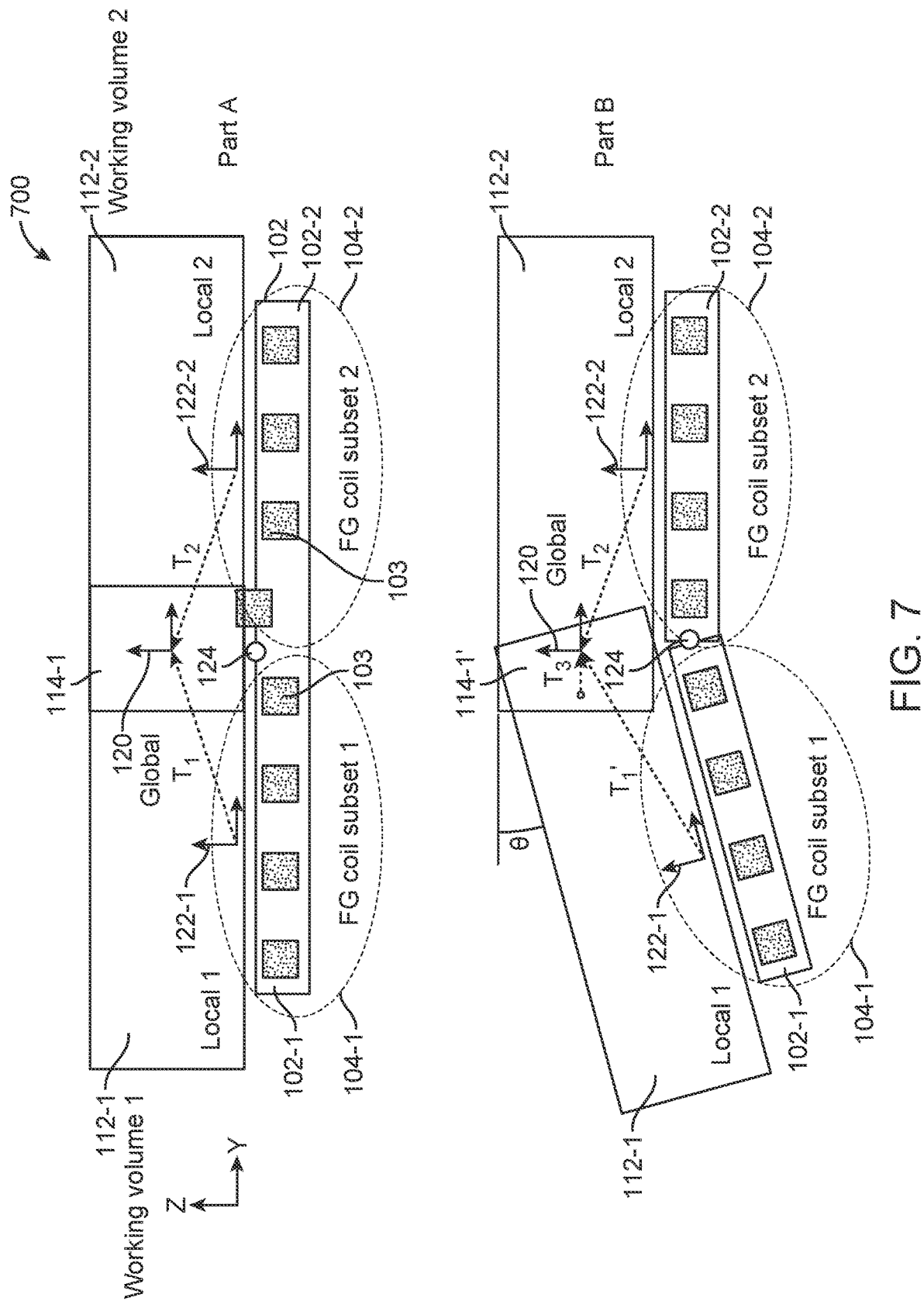
FIG. 7 illustrates schematic views of an EM tracking surgical system having reconfigurable bed portions, in accordance with some embodiments.

Although FIG. 7 illustrates the tracking of a surgical tool having a plurality of position sensors, one of ordinary skill in the art would appreciate that the EM system can also be used to track a plurality of surgical tools having a plurality of position sensors. Each surgical tool may have one or multiple position sensors.

7. EM Tracking Surgical Systems Having Reconfigurable Bed Portions

FIG. 7 illustrates schematic views of an EM tracking surgical system having reconfigurable bed portions, in accordance with some embodiments. Part A of FIG. 7 illustrates a side view of a portion of an EM tracking surgical system 700 when a surgical bed is in a first position. Part B of FIG. 7 illustrates the side view of the system 700 when the surgical bed is in a second position.

As shown in FIG. 7, a surgical bed 102 may comprise reconfigurable bed portions that can move relative to each other. For example, the surgical bed 102 may comprise a first bed portion 102-1 and a second bed portion 102-2 connected at a hinge 124 that allows the bed portions to move (for example, but not limited to, rotate and/or slide) relative to each other. A first subset of field generator coils 104-1 may be embedded along a length of the first bed portion 102-1. A second subset of field generator coils 104-2 may be embedded along a length of the second bed portion 102-2. Accordingly, the first and second subsets of field generator coils 104 may be embedded along a length portion of the surgical bed 102.

A first working volume 112-1 may be defined above the first subset of field generator coils 104-1, and a second working volume 112-2 may be defined above the second subset of field generator coils 104-2, similar to the embodiment previously described in FIG. 4. In some embodiments, the dimensions and/or size of the first and second working volumes 112-1 and 112-2 may be the same. Alternatively, the dimensions and/or size of the first and second working volumes 112-1 and 112-2 may be different.

As shown in FIG. 7, the first and second working volumes may overlap so as to form a first overlapping working volume 114-1 disposed at a boundary between the first and second subsets of field generator coils 104-1 and 104-2. The first and second working volumes 112-1 and 112-2 may be configured to overlap by various amounts. For example, the first and second working volumes 112-1 and 112-2 may be configured to overlap by 1%, 2%, 5%, 10%, 15%, 20%, 25%, 30%, or more than 30%. The first and second working volumes 112-1 and 112-2 may be configured to overlap such that one or more position sensors, such as position sensors 116 discussed above, can be accurately tracked and controlled near the boundaries of the control volumes 112, and as the position sensor(s) 116 moves between adjacent working volumes 112.

Each subset of field generator coils 104 may comprise a number of field generator coils 103. The number of field generator coils 103 in the subsets 104 may be same or different. In FIG. 7, each subset of field generator coils 104 may comprise eight field generator coils 103, for example similar to the embodiment previously described in FIG. 4. The field generator coils 103 may be disposed along the edges of the surgical bed 102 in two parallel rows (not shown in FIG. 7). The field generator coils 103 may be spaced apart from one another along each row (for example, but not limited to, at a pitch p in the Y-direction). Laterally opposite field generator coils 103 in the two rows may be spaced apart (for example, but not limited to, by a distance d) from each other in the X-direction. The field generator coils 103 in the subsets 104 may be spaced in a configuration that allows an EM field of a predetermined strength to substantially extend over each working volume 112.

As shown in FIG. 7, a global coordinate system 120 may be defined above a center portion of the surgical bed 102. For example, the global coordinate system 120 may be defined above a boundary line between the first bed portion 102-1 and the second bed portion 102-2. An origin of the global coordinate system 120 may lie above the center portion of the surgical bed 102 along the Z-direction. The origin of the global coordinate system 120 may also lie at a predetermined location above the hinge 124 when the surgical bed is in the position shown in part A of FIG. 7. The origin of the global coordinate system 120 may serve as a datum point from which the positions of a patient's body, the subsets of field generator coils 104, and the working volume 112 may be defined.

A first local coordinate system 122-1 may be defined above a center portion of the first bed portion 102-1. Likewise, a second local coordinate system 122-2 may be defined above a center portion of the second bed portion 102-2. The first local coordinate system 122-1 may or may not have an origin that lies at a center portion of the first working volume 112-1. Similarly, the second local coordinate system 122-2 may or may not have an origin that lies at a center portion of the second working volume 112-2. For example, as shown in part A of FIG. 7, the origin of the first local coordinate system 122-1 may lie below the center portion of the first working volume 112-1, and in close proximity to the first bed portion 102-1. Likewise, the origin of the second local coordinate system 122-2 may lie below the center portion of the second working volume 112-2, and in close proximity to the second bed portion 102-2.

Vectors may be defined between the global coordinate system 120 and the local coordinate systems 122-1 and 122-2. For example, a vector T1 may be defined from the origin of the first local coordinate system 122-1 to the origin to the global coordinate system 120. A vector T2 may be defined from the origin of the second local coordinate system 122-2 to the origin to the global coordinate system 120. In some embodiments, another vector (not shown) may be defined from the origin of the first local coordinate system 122-1 to the origin of the second local coordinate system 122-2. The vectors T1 and T2 may be used to define the spatial relationship between the first working volume 112-1 and the second working volume 112-2. In particular, the vectors T1 and T2 may be used to define the spatial relationship between the first and second working volumes 112-1 and 112-2 relative to the datum point (for example, but not limited to, origin of the global coordinate system 120) as the first and second bed portions 102-1 and 102-2 move relative to each other.

As shown in part A of FIG. 7, the first bed portion 102-1 and the second bed portion 102-2 may initially lie on a same horizontal plane extending along the Y-axis direction. The first and second bed portions 102-1 and 102-2 may be configured to move relative to each other. For example, as shown in part B of FIG. 7, the first bed portion 102-1 may rotate by an angle θ in a clockwise direction about an X-axis extending through the hinge 124. The first bed portion 102-1 may be rotated, for example, to lower or raise a portion of a patient's body that is supported by the first bed portion 102-1. Since the first control volume 112-1 is defined by the EM field generated by the first subset of field generator coils 104-1, the first control volume 112-1 may also rotate by the angle θ in a clockwise direction about the X-axis. As shown in part B of FIG. 7, it may be observed that the origin of the first local coordinates system 122-1 has shifted to a new location. Accordingly, a new vector T1' may be defined from the shifted origin of the first local coordinates system 122-1 to the origin of the global coordinates system 120, whereby the vector T1' is different from the vector T1. Since the second bed portion 102-2 is not rotated relative to the global coordinates system 120, the origin of the second local coordinates system 122-2 remains unchanged, and therefore the vector T2 remains the same. The vectors T1' and T2 may be used to define the spatial relationship between the first and second working volumes 112-1 and 112-2 relative to the datum point (for example, but not limited to, origin of the global coordinate system 120) after the first bed portion 102-1 has moved relative to the second bed portion 102-2.

Although part B of FIG. 7B illustrates movement of the first bed portion 102-1 relative to the second bed portion 102-2, the movement between the bed portions is not limited thereto. For example, in some embodiments, the second bed portion 102-2 may move relative to the first bed portion 102-1. Optionally, the first and second bed portions 102-1 and 102-2 may simultaneously move relative to each other such that the origins of the first and second local coordinate systems shift to different locations. The relative movement between the bed portions 102-1 and 102-2 may comprise a rotational motion, a translational motion, and/or a combination of rotational and translational motion, about one or more axes. Accordingly, relative movement of the bed portions 102-1 and 102-2 in one or more degrees of freedom (for example, but not limited to, six degrees of freedom) may be contemplated.

In some embodiments, a position, shape, and/or size of the overlapping working volume 114 between adjacent working volumes may change when the bed portions move relative to each other. For example, as shown in part A of FIG. 7, a center (or centroid) of the first overlapping working volume 114-1 may be located at the origin of the global coordinates system 120. The first overlapping working volume 114-1 may have a regular shape (for example, but not limited to, defined by a length U1, width W, and height H, similar to the embodiment previously shown in FIG. 4).

When the first bed portion 102-1 rotates relative to the second bed portion 102-2, the position, shape, and/or size of the first overlapping working volume 114-1 may change. For example, as shown in part B of FIG. 7, the first overlapping working volume 114-1 may transform to overlapping working volume 114-1' having an irregular shape (for example, but not limited to, having a trapezoidal-like profile as viewed from a side of the overlapping working volume 114-1'). The origin of the global coordinates system 120 remains unchanged by the relative rotation of the bed portions. Unlike part A of FIG. 7, the center (or centroid) of the overlapping working volume 114-1' is not located at the origin of the global coordinates system 120 after the rotation. Instead, the center (or centroid) of the overlapping working volume 114-1' may be offset from the origin of the global coordinates system 120 by a vector T3 after the rotation.

Figure 8:
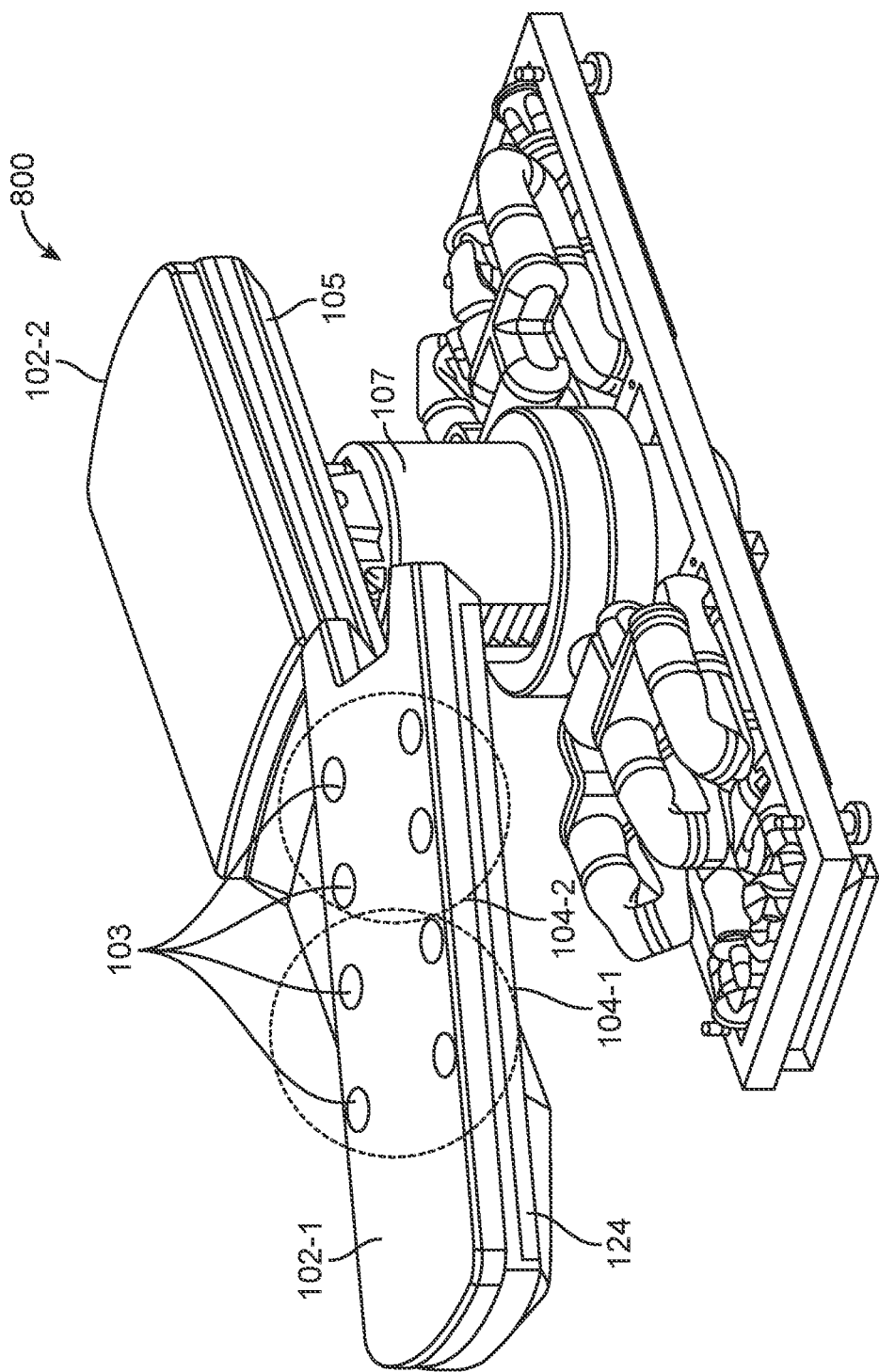
FIG. 8 illustrates a perspective view of an EM tracking surgical system having a reconfigurable bed portion, in accordance with some embodiments.

FIG. 8 illustrates a perspective view of an EM tracking surgical system having a reconfigurable bed portion, in accordance with some embodiments. As shown in FIG. 8, an EM tracking surgical system 800 may comprise a surgical bed 102 having a reconfigurable bed portion that is movable move relative to a fixed bed portion. For example, the surgical bed 102 may comprise a first bed portion 102-1 and a second bed portion 102-2 that are disposed on a base 105. The base 105 may be supported by a stand 107. The first bed portion 102-1 may be operably connected to a first portion of the base 105 via a hinge 124. The hinge 124 may be disposed at a distal portion of the surgical bed 102 and/or the base 105. The second bed portion 102-2 may be rigidly attached to a second portion of the base 105. In some embodiments, the second bed portion 102-2 may be integrally formed with the base 105. The hinge 124 may allow movement (for example, but not limited to, rotational and/or translational) of the bed portions relative to each other. For example, the first bed portion 102-1 may be configured to rotate about the hinge 124, such that the first bed portion 102-1 is rotatable relative to the second bed portion 102-2.

A plurality of field generator coils 103 may be embedded or integrated along edge portions of the surgical bed 102. For example, as shown in FIG. 8, the plurality of field generator coils 103 may be embedded in two parallel rows along a length of the first bed portion 102-1. The plurality of field generator coils 103 may be positioned along the edges of the first bed portion 102-1, so as to allow for unobstructed use of fluoroscopy when a patient is placed on the first bed portion 102-1. Optionally, in some embodiments (not shown), a plurality of field generator coils may be further embedded along a length of the second bed portion 102-2 in two parallel rows.

The plurality of field generator coils 103 may include and can be grouped into subsets. For example, as shown in FIG. 8, the field generator coils 103 may include a first subset of field generator coils 104-1 and a second subset of field generator coils 104-2. Although two subsets are illustrated in FIG. 8, it should be noted that the invention is not limited thereto, and that any number of subsets may be contemplated.

Each subset of field generator coils 104 may comprise a number of field generator coils 103. In the example of FIG. 8, each subset of field generator coils 104 may comprise four field generator coils 103. However, a subset of field generator coils need not be limited to four field generator coils. In some embodiments, a subset of field generator coils may comprise more than four field generator coils. In other embodiments, a subset of field generator coils may comprise less than four field generator coils. Any number of field generator coils within each subset may be contemplated.

Figure 9A:
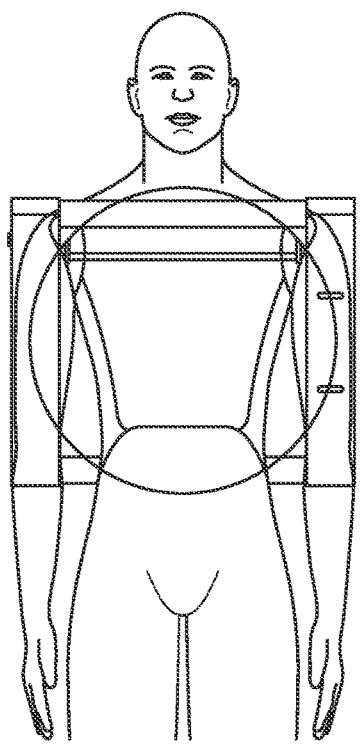
FIGS. 9A and 9B illustrate sizing of a reconfigurable bed portion of an EM tracking surgical system based on exemplary dimensions of a human torso, in accordance with some embodiments.
Figure 9B:
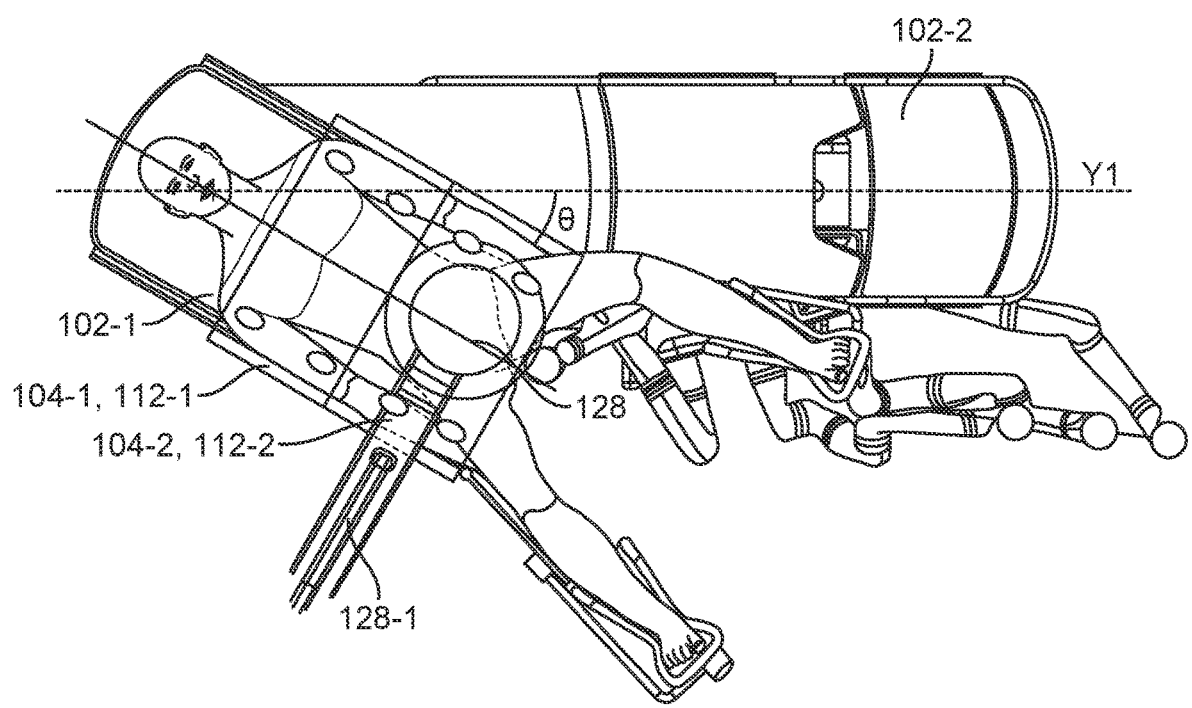

FIGS. 9A and 9B illustrate sizing of a reconfigurable bed portion of an EM tracking surgical system based on exemplary dimensions of a human torso, in accordance with some embodiments. FIG. 9A illustrates exemplary dimensions of a human torso and a working volume that is defined based on those exemplary dimensions. FIG. 9B illustrates a schematic view of a patient who is placed on a reconfigurable bed portion of an EM tracking surgical system.

FIG. 9A illustrates exemplary dimensions of a human torso. For example, a length of a longest human torso (for example, but not limited to, as measured from neck to anus) may be about 32.9 inches, and a width of the human torso may be about 13 inches. A working volume of each subset of field generator coils may be defined based on those dimensions.

Referring to FIG. 9B, a patient may be placed on the first bed portion 102-1 of the surgical bed 102 shown in FIG. 8. As shown in FIG. 9B, the first bed portion 102-1 may be rotated relative to the second bed portion 102-2, such that the patient's body is rotated an angle $\theta$ relative to a longitudinal axis Y1 extending longitudinally along the second bed portion 102-2.

A first working volume 112-1 and a second working volume 112-2 may be associated with the first subset of field generator coils 104-1 and the second subset of field generator coils 104-2, respectively. In some embodiments, the first working volume 112-1 may be a cylinder. The diameter of the cylinder may be about 5", 6", 7", 8", 9", 10", 11", 12", 13", 14", 15", 16" 17", 18", 19", 20", 21", 22", 23", 24", 25", or greater than 25". The height of the cylinder may be about 5", 6", 7", 8", 9", 10", 11", 12", 13", 14", 15", 16" 17", 18", 19", 20", 21", 22", 23", 24", 25", or greater than 25". In some examples, a cylinder may have a minimum diameter and height of about 5"×5". In other examples, a cylinder may have a maximum distance and height of about 25"×25". Optionally, in some examples, each of the diameter and height of a cylinder may be less than 5", or greater than 25". Optionally, the first working volume 112-1 may be a cuboid. The length of the cuboid may be about 5", 6", 7", 8", 9", 10", 11", 12", 13", 14", 15", 16" 17", 18", 19", 20", 21", 22", 23", 24", 25", or greater than 25". The width of the cuboid may be about 5", 6", 7", 8", 9", 10", 11", 12", 13", 14", 15", 16" 17", 18", 19", 20", 21", 22", 23", 24", 25", or greater than 25". The height of the cuboid may be about 5", 6", 7", 8", 9", 10", 11", 12", 13", 14", 15", 16" 17", 18", 19", 20", 21", 22", 23", 24", 25", or greater than 25". In some examples, a cuboid may have a minimum length, width, and height of about 5"×5"×5". In other examples, a cuboid may have a maximum length, width, and height of about 25"×25"×25". Optionally, in some examples, each of the length, width, and height of a cuboid may be less than 5", or greater than 25". The second working volume 112-2 may or may not have the same shape and/or dimensions as the first working volume 112-1. Any shape and/or dimensions for the first and second working volumes may be contemplated.

As shown in FIG. 9B, a fluoroscopic imaging system 128 may be placed above the patient's body. For example, the fluoroscopic imaging system 128 may be placed within or above the second working volume 112-2. The fluoroscopic imaging system 128 may be supported by a mechanical arm 128-1 extending towards and/or over the first bed portion 102-1. In the example of FIG. 9B, the fluoroscopic imaging system 128 may be used to capture fluoroscopic images of the patient's body within the second working volume 112-2. Since the second subset of field generator coils 104-2 is placed along the edges of the second bed portion 102-2, a central portion of the surgical bed may be free enough of effects from the field generates such that fluoroscopy can be used with little or no obstruction.

FIG. 10 illustrates a reconfigurable bed portion of an EM tracking surgical system, in accordance with some embodiments. As previously described in FIGS. 8, 9A, and 9B, a surgical bed 102 may comprise a first bed portion 102-1 and a second bed portion 102-2 that may be disposed on a base 105. The first bed portion 102-1 may be operably connected to a hinge 124 that allows the first bed portion 102-1 to move (for example, but not limited to, rotate and/or translate) relative to the second bed portion 102-2.

As shown in FIG. 10, a first bed portion 102-1 may have a length l and a width w. In some embodiments, the length l may be about 29.5 inches, and the width w may be about 18.5 inches. In some embodiments, a cutout 130 may be formed at an end of first bed portion 102-1, so as to prevent mechanical interference as the first bed portion 102-1 moves relative to the second bed portion 102-2. In the example of FIG. 10, the cutout 130 may have a trapezoidal shape, and may be offset by a distance s from an edge portion of the first bed portion 102-1.

The first bed portion 102-1 may further include two parallel rows 106 on its edges. As previously described, by placing a plurality of field generator coils along the two parallel rows 106 on the edges of the surgical bed 102 (for example, but not limited to, the first bed portion 102-1), unobstructed use of fluoroscopy can be achieved to image at least a portion of a patient's body. Each row 106 may have a width of t that is associated with an area of fluoro obstruction. In some embodiments, the width t may be less than or equal to about 2 inches. It should be noted that rows 106 constitute areas of fluoroscopy obstruction, since the field generator coils are radio-opaque.

Figure 11:
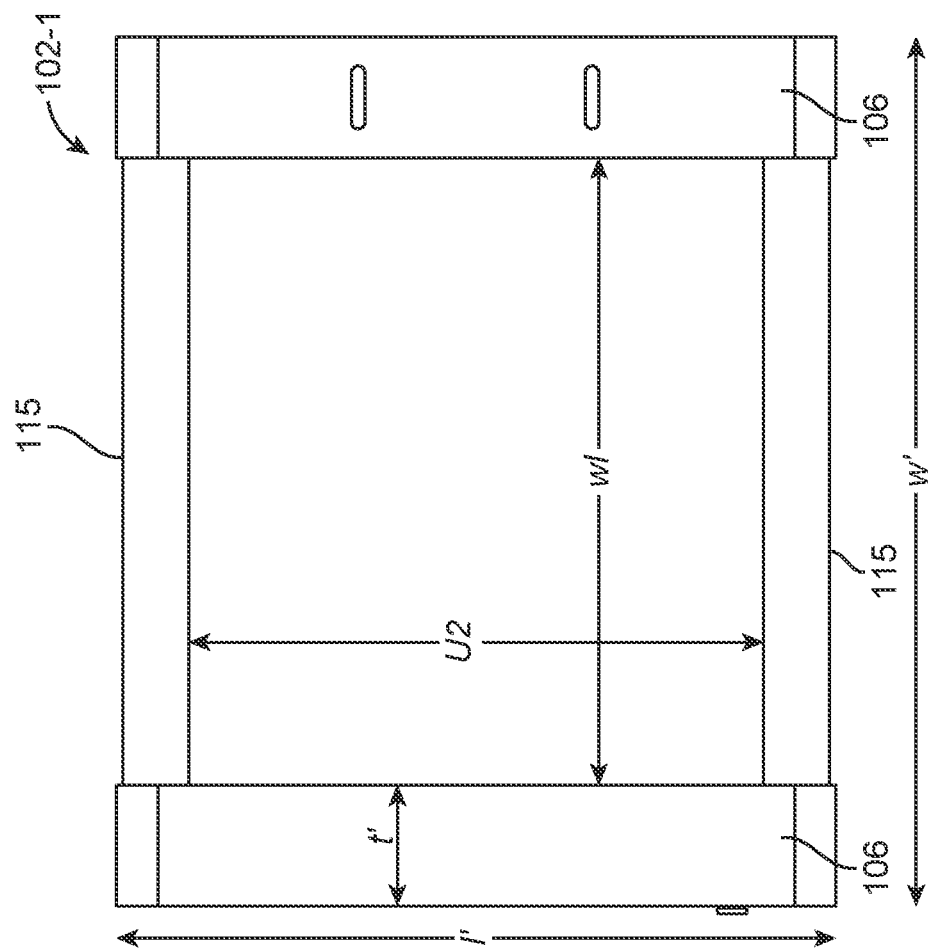
FIG. 11 illustrates dimensions and locations of field generator coils on a reconfigurable bed portion of an EM tracking surgical system, in accordance with some embodiments.

FIG. 11 illustrates dimensions and locations of field generator coils on a reconfigurable bed portion of an EM tracking surgical system, in accordance with some embodiments. In the example of FIG. 11, a reconfigurable bed portion 102-1 of a surgical bed may have a length l' and a width w'. In some embodiments, the length l' may be about 18.1 inches, and the width w' may be about 21.8 inches.

The bed portion 102-1 may further include two parallel rows 106 on its edges. As previously described, by placing a plurality of field generator coils along two parallel rows on the edges of the surgical bed, unobstructed use of fluoroscopy can be achieved to image at least a portion of a patient's body. Each row 106 may have a width of t'. In some embodiments, the width t' may be less than or equal to about 3.025 inches. The two parallel rows 106 may be separated by a distance w1. In some embodiments, the distance w1 may be about 15.75 inches. Additionally, rows 106 may constitute areas of fluoroscopy obstruction, since the field generator coils are radio-opaque.

As shown in FIG. 11, end portions 115 of the bed portion 102-1 may correspond to regions where adjacent working volumes overlap. The end portions 114 may be separated by a distance U2. In some embodiments, the distance U2 may be about 14.5 inches.

Figure 12:
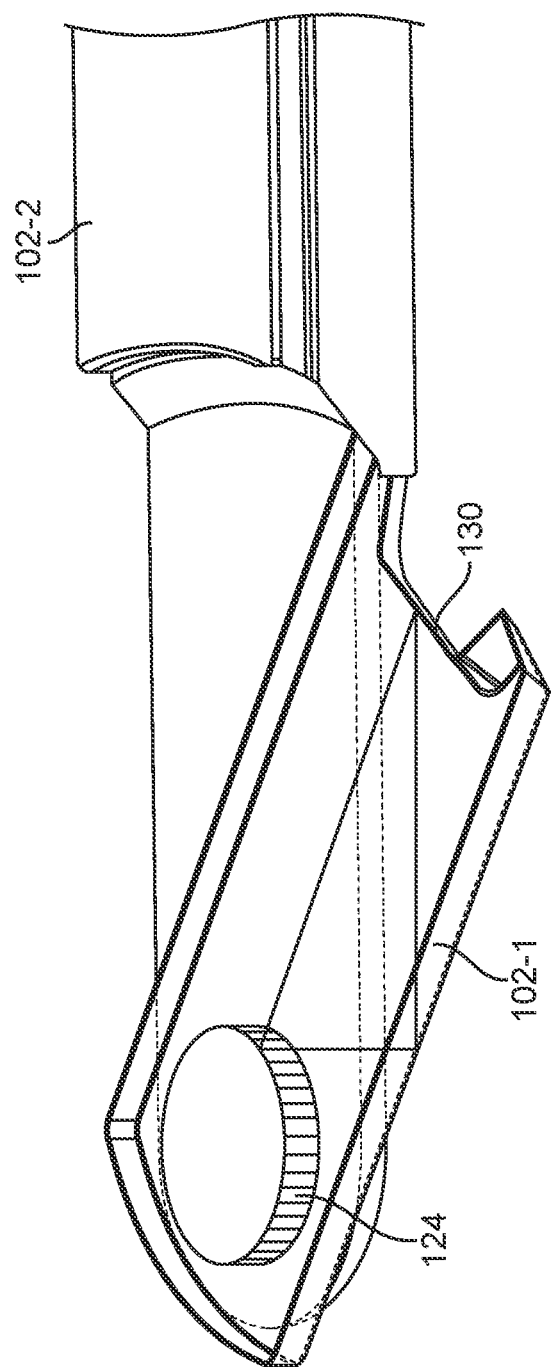
FIG. 12 illustrates an estimated length of a working volume based on the dimensions of a reconfigurable bed portion of an EM tracking surgical system, in accordance with some embodiments.

FIG. 12 illustrates an estimated length of a working volume based on the dimensions of a reconfigurable bed portion of an EM tracking surgical system, in accordance with some embodiments. As shown in FIG. 12, a distance from an edge of a hinge bearing 124 to an edge of a cutout 130 of a first bed portion 102-1 may be denoted by l1. The distance l1 may be indicative of a length of a total working volume above the first bed portion 102-1. In some embodiments, the distance l1 may be about 26.5 inches. FIG. 12 also illustrates first bed portion 102-1 angled with respect to second bed portion 102-2.

Figure 13:
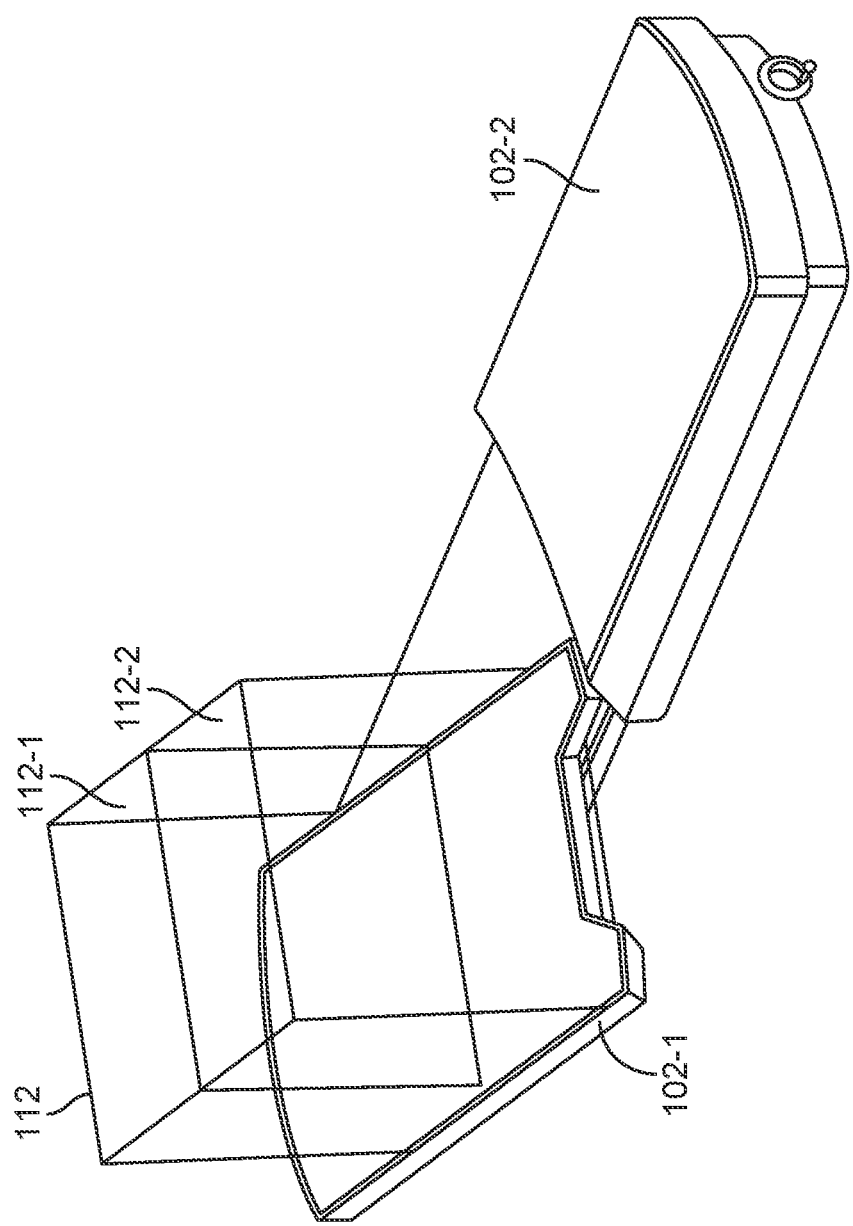
FIG. 13 illustrates an exemplary working volume above a reconfigurable bed portion of an EM tracking surgical system, in accordance with some embodiments.

FIG. 13 illustrates an exemplary working volume above a reconfigurable bed portion of an EM tracking surgical system, in accordance with some embodiments. As shown in FIG. 13, a total working volume 112 may be defined above a first bed portion 102-1 of a surgical bed 102. In FIG. 13, first bed portion 102-1 is shown angled with respect to second bed portion 102-2. The total working volume 112 may comprise a first working volume 112-1 and a second working volume 112-2. The total working volume 112 may have a length $L_T$, a width W, and a height H. In some embodiments, the length LT may be about 31 inches, the width W may be about 19 inches, and the height H may be about 19.7 inches. It should be noted that the invention is not limited thereto, and that any dimensions of the total working volume may be contemplated. As previously described, the first working volume 112-1 and the second working volume 112-2 may overlap, which can help to minimize deadzones (for example, but not limited to, places where a position sensor cannot be tracked, either due to a weak EM field or EM interference).

As used herein A and/or B encompasses one or more of A or B, and combinations thereof such as A and B. It will be understood that although the terms "first," "second," "third" etc. may be used herein to describe various elements, components, regions and/or sections, these elements, components, regions and/or sections should not be limited by these terms. These terms are merely used to distinguish one element, component, region or section from another element, component, region or section. Thus, a first element, component, region or section discussed below could be termed a second element, component, region or section without departing from the teachings of the present invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including," when used in this specification, specify the presence of stated features, regions, integers, steps, operations, elements and/or components, but do not preclude the presence or addition of one or more other features, regions, integers, steps, operations, elements, components and/or groups thereof.

Furthermore, relative terms, such as "lower" or "bottom" and "upper" or "top" may be used herein to describe one element's relationship to other elements as illustrated in the figures. It will be understood that relative terms are intended to encompass different orientations of the elements in addition to the orientation depicted in the figures. For example, if the element in one of the figures is turned over, elements described as being on the "lower" side of other elements would then be oriented on the "upper" side of the other elements. The exemplary term "lower" can, therefore, encompass both an orientation of "lower" and "upper," depending upon the particular orientation of the figure. Similarly, if the element in one of the figures were turned over, elements described as "below" or "beneath" other elements would then be oriented "above" the other elements. The exemplary terms "below" or "beneath" can, therefore, encompass both an orientation of above and below.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. Numerous different combinations of embodiments described herein are possible, and such combinations are considered part of the present disclosure. In addition, all features discussed in connection with any one embodiment herein can be readily adapted for use in other embodiments herein. It is intended that the following claims define the scope of the invention and that methods and structures within the scope of these claims and their equivalents be covered thereby.

What is claimed is:

1. An instrument tracking system comprising:
   a first set of one or more electromagnetic (EM) field generators associated with a first structure and configured to generate a first EM field volume;
   a second set of one or more EM field generators associated with a second structure and configured to generate a second EM field volume, the second EM field volume overlapping the first EM field volume in an overlapping EM field volume; and
   controller circuitry configured to:
      determine a first spatial relationship between the first EM field volume and the second EM field volume relative to a global coordinate system;
      after movement of the first structure relative to the second structure, determine a modified spatial relationship between the first EM field volume and the second EM field volume relative to the global coordinate system;
      detect a position sensor within the first EM field volume, the position sensor being associated with an instrument; and
      in response to said detecting the position sensor within the first EM field volume, activate the first set of one or more EM field generators.

2. The system of claim 1, wherein:
   the first EM field volume is associated with a first local coordinate system defined above a center portion of the first structure;
   the second EM field volume is associated with a second local coordinate system defined above a center portion of the second structure; and
   the modified spatial relationship between the first EM field volume and the second EM field volume is based on at least one of:

a first vector between the first local coordinate system and the global coordinate system; or
a second vector between the second local coordinate system and the global coordinate system.

3. The system of claim 2, wherein the global coordinate system lies above a hinge between the first structure and the second structure.

4. The system of claim 2, wherein the first local coordinate system and the second local coordinate system have origin points in space that are lower than an origin point of the global coordinate system.

5. The system of claim 1, wherein the controller circuitry is further configured to determine vectors between local coordinate systems of the first and second EM field volumes, respectively, and the global coordinate system.

6. The system of claim 1, wherein:
said movement of the first structure is a rotational movement relative to the second structure; and
the modified spatial relationship between the first EM field volume and the second EM field volume indicates an offset angle between the first EM field volume and the second EM field volume.

7. The system of claim 1, wherein:
prior to said movement of the first structure relative to the second structure, the overlapping EM field volume has a rectangular side profile shape; and
after said movement of the first structure relative to the second structure, the overlapping EM field volume has a non-rectangular side profile shape.

8. The system of claim 7, wherein the non-rectangular side profile shape is a trapezoidal shape.

9. An instrument tracking system comprising:
a first set of one or more electromagnetic (EM) field generators associated with a first surgical bed portion of a surgical bed and configured to generate a first EM field volume;
a second set of one or more EM field generators associated with a second surgical bed portion of the surgical bed and configured to generate a second EM field volume, the second EM field volume overlapping the first EM field volume in an overlapping EM field volume; and
controller circuitry configured to:
determine a first vector between a first local coordinate system associated with the first EM field volume and a global coordinate system;
determine a second vector between a second local coordinate system associated with the second EM field volume and the global coordinate system; and
after relative movement between the first surgical bed portion and the second surgical bed portion, determine a modified first vector between the first local coordinate system and the global coordinate system.

10. The system of claim 9, wherein:
prior to said relative movement between the first surgical bed portion and the second surgical bed portion, a center of the overlapping EM field volume is located at an origin of the global coordinate system; and
after said relative movement between the first surgical bed portion and the second surgical bed portion, the center of the overlapping EM field volume is offset from the origin of the global coordinate system.

11. The system of claim 10, wherein the controller circuitry is further configured to determine a third vector representing an offset between the center of the overlapping EM field volume and the origin of the global coordinate system.

12. The system of claim 11, wherein the global coordinate system is defined above a center portion of the surgical bed.

13. The system of claim 9, wherein the controller circuitry is further configured to define a position of a patient relative to an origin of the global coordinate system.

14. The system of claim 9, wherein:
the first local coordinate system is defined above a center portion of the first surgical bed portion; and
the second local coordinate system is defined above a center portion of the second surgical bed portion.

15. A method of tracking an instrument, the method comprising:
determining, relative to a global coordinate system, a first spatial relationship between a first electromagnetic (EM) field volume associated with a first structure and a second EM filed volume associated with a second structure;
after movement of the first structure relative to the second structure, determining a modified spatial relationship between the first EM field volume and the second EM field volume relative to the global coordinate system;
detecting a first position sensor of a set of one or more position sensors within a first electromagnetic (EM) field volume associated with a first set of EM field generators, the first position sensor being associated with an instrument;
in response to said detecting the first position sensor within the first EM field volume, activating the first set of EM field generators;
detecting the first position sensor in an overlapping EM field volume where the first EM field volume overlaps with a second EM field volume associated with a second set of EM field generators; and
in response to said detecting the first position sensor in the overlapping EM field volume, activating the second set of EM field generators.

16. The method of claim 15, wherein, when the second set of EM field generators is activated, the first set of EM field generators remains activated while the first position sensor is disposed within the overlapping EM field volume.

17. The method of claim 16, further comprising:
after said activating the second set of EM field generators:
detecting the first position sensor within the second EM field volume outside of the overlapping EM field volume; and
determining that none of the set of one or more position sensors is disposed in the first EM field volume; and
in response to said detecting the first position sensor within the second EM field volume outside of the overlapping EM field volume and said determining that none of the set of one or more position sensors is disposed in the first EM field volume, deactivating the first set of EM field generators.

18. The method of claim 15, wherein the modified spatial relationship between the first EM field volume and the second EM field volume is based on a first vector between the first EM field volume and the global coordinate system and a second vector between the second EM field volume and the global coordinate system.

19. The method of claim 15, wherein:
prior to said movement of the first structure relative to the second structure, the overlapping EM field volume has a regular shape; and
after said movement of the first structure relative to the second structure, the overlapping EM field volume has an irregular shape.

20. The method of claim 19, wherein the regular shape is an elliptical, cylindrical, or cubic shape.

\* \* \* \* \*